(12) United States Patent
Degertekin et al.

(10) Patent No.: US 9,310,485 B2
(45) Date of Patent: Apr. 12, 2016

(54) COMPACT, ENERGY-EFFICIENT ULTRASOUND IMAGING PROBES USING CMUT ARRAYS WITH INTEGRATED ELECTRONICS

(75) Inventors: F. Levent Degertekin, Atlanta, GA (US); Mustafa Karaman, Istanbul (TR)

(73) Assignee: Georgia Tech Research Corporation, Atlanta, GA (US)

( * ) Notice: Subject to any disclaimer, the term of this patent is extended or adjusted under 35 U.S.C. 154(b) by 820 days.

(21) Appl. No.: 13/471,426

(22) Filed: May 14, 2012

(65) Prior Publication Data
US 2013/0128702 A1 May 23, 2013

Related U.S. Application Data

(60) Provisional application No. 61/485,414, filed on May 12, 2011, provisional application No. 61/485,417, filed on May 12, 2011, provisional application No. 61/485,423, filed on May 12, 2011.

(51) Int. Cl.
*H04R 9/00* (2006.01)
*G01S 15/89* (2006.01)
*A61B 8/00* (2006.01)
*A61B 8/12* (2006.01)
(Continued)

(52) U.S. Cl.
CPC . *G01S 15/89* (2013.01); *A61B 8/12* (2013.01); *A61B 8/445* (2013.01); *A61B 8/4488* (2013.01); *A61B 8/4494* (2013.01); *B06B 1/0292* (2013.01); *G01S 15/8913* (2013.01); *G01S 15/8925* (2013.01); *G01S 15/8927* (2013.01); *G01S 7/5208* (2013.01); *G01S 7/52047* (2013.01); *G01S 15/8922* (2013.01); *G01S 15/8993* (2013.01)

(58) Field of Classification Search
CPC .............................. B06B 1/0292; B06B 1/0625
USPC .......................................................... 367/181
See application file for complete search history.

(56) References Cited

U.S. PATENT DOCUMENTS

| 5,351,691 A | 10/1994 | Brommersma |
| 5,857,974 A | 1/1999 | Eberle et al. |
| 6,049,958 A | 4/2000 | Eberle et al. |

(Continued)

FOREIGN PATENT DOCUMENTS

| WO | 2009073752 | 6/2009 |
| WO | 2009073753 | 6/2009 |

*Primary Examiner* — Mark Hellner
(74) *Attorney, Agent, or Firm* — Troutman Sanders LLP; Ryan A. Schneider; Benjamin C. Wiles

(57) ABSTRACT

A CMUT on CMOS imaging chip is disclosed. The imaging chip can use direct connection, CMOS architecture to minimize external connections and minimize chip cross-section. The CMOS architecture can enable substantially the entire chip area to be utilized for element placement. The chip can utilize arbitrarily selected transmit (Tx) and receive (Rx) element arrays to improve image quality, while reducing sampling time. The chip can comprise a plurality of dummy elements dispersed throughout the Tx and Rx elements to reduce cross-talk. The chip can utilize batch firing techniques to increase transmit power using sparse Tx arrays. The chip can comprise hexagonal Tx and or Rx subarrays for improved image quality with reduce sample sizes. The chip can utilize electrode geometry, bias voltage, and polarity to create phased and amplitude apodized arrays of Tx and Rx elements.

20 Claims, 21 Drawing Sheets

(51) Int. Cl.
   *B06B 1/02*      (2006.01)
   *G01S 7/52*      (2006.01)

(56) References Cited

U.S. PATENT DOCUMENTS

| | | | |
|---|---|---|---|
| 6,120,454 A | 9/2000 | Suorsa et al. | |
| 6,299,580 B1 | 10/2001 | Asafusa | |
| 6,497,667 B1 | 12/2002 | Miller et al. | |
| 6,503,204 B1 * | 1/2003 | Sumanaweera et al. | 600/459 |
| 6,589,182 B1 | 7/2003 | Loftman et al. | |
| 6,623,432 B2 | 9/2003 | Powers et al. | |
| 6,865,140 B2 | 3/2005 | Thomenius et al. | |
| 6,899,682 B2 | 5/2005 | Eberle et al. | |
| 7,052,464 B2 | 5/2006 | Wodnicki | |
| 7,088,830 B2 | 8/2006 | Norris et al. | |
| 7,221,077 B2 | 5/2007 | Sawada | |
| 7,427,825 B2 | 9/2008 | Frey et al. | |
| 7,460,439 B2 | 12/2008 | Moon et al. | |
| 7,514,851 B2 | 4/2009 | Wilser et al. | |
| 7,559,897 B2 | 7/2009 | Cerofolini | |
| 7,732,992 B2 | 6/2010 | Wilser et al. | |
| 7,745,973 B2 * | 6/2010 | Bayram et al. | 310/328 |
| 2007/0167814 A1 | 7/2007 | Wakabayashi et al. | |
| 2009/0270735 A1 | 10/2009 | Cerofolini | |
| 2012/0071761 A1 * | 3/2012 | Miller | 600/459 |

* cited by examiner

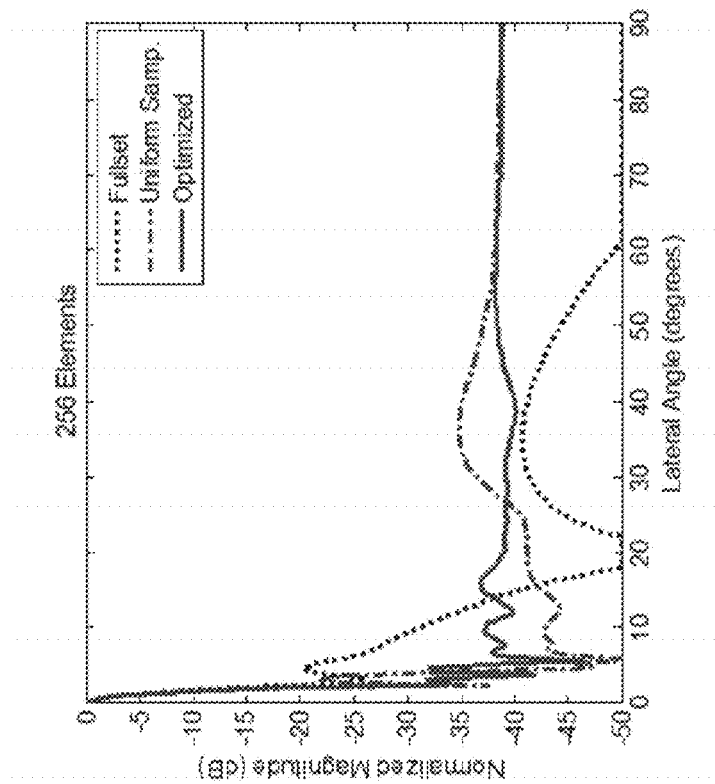
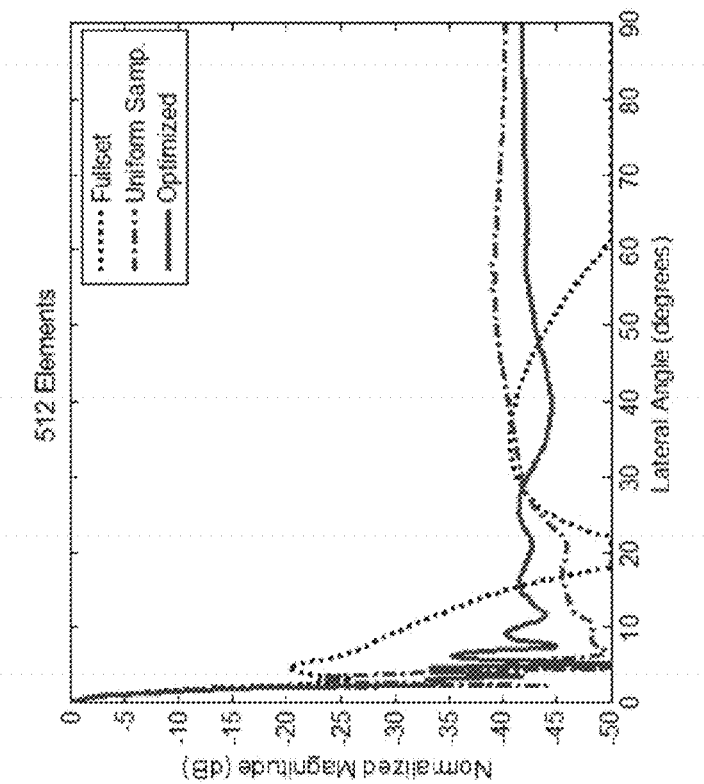
Fig. 14d

COMPACT, ENERGY-EFFICIENT ULTRASOUND IMAGING PROBES USING CMUT ARRAYS WITH INTEGRATED ELECTRONICS

CROSS-REFERENCE TO RELATED APPLICATIONS AND PRIORITY CLAIM

This application claims priority under 35 U.S.C. §119(e) to, and the benefit of, U.S. Provisional Patent Application No. 61/485,414, entitled "Single Chip CMUT-on-CMOS Arrays for Forward-Looking Intravascular and Intracardiac Imaging," U.S. Provisional Patent Application No. 61/485,417, entitled "Hexagonal Ring Arrays for Forward-Looking Intravascular and Intracardiac Imaging," and U.S. Provisional Patent Application No. 61/485,423, entitled "Donut Sparse CMUT arrays for Forward-Looking Volumetric Imaging Catheter Probes," all of which were filed 12 May 2011. The entireties of the above-mentioned applications are hereby incorporate by reference as if set forth in its entirety below.

STATEMENT REGARDING FEDERALLY SPONSORED RESEARCH

This invention was made with government support under Contract E25-C54 awarded by the National Institutes of Health. The government has certain rights in the invention.

BACKGROUND OF THE INVENTION

1. Field of the Invention

Embodiments of the present invention relate to ultrasound imaging probes, and particularly, to flexible, single chip, CMUT based ultrasound imaging probes using various monolithically integrated CMUT arrays on CMOS electronics.

2. Background of Related Art

Side-looking intravascular ultrasound ("IVUS") imaging probes exist that provide relatively high resolution images of tissue and fluid. This can be useful, for example, when inspecting the inside surfaces of vessels or tissues immediately surrounding the vessel. Similarly, intracardiac echocardiography ("ICE") probes also exist which use one-dimensional (1-D) imaging arrays.

Unfortunately, current commercial IVUS imaging systems offer only side-looking capabilities and cannot generate images of, for example, the volume in front of the catheter. ICE probes, for example, provide only two-dimensional cross sections, but not volumetric images. The ability to image fluid and/or tissue directly in front of the probe can be useful in a number of applications. An IVUS catheter that can provide forward-looking (FL) volumetric ultrasound images would be a valuable clinical tool for, for example and not limitation, guiding interventions in coronary arteries, for the treatment of chronic total, or near-total, vascular occlusions, and for stent deployment. See, e.g., FIGS. 1a-1b.

In order to navigate tortuous arteries and coronary structures, for example, an important aspect of IVUS and ICE probes is the size and flexibility of the probes. As a result, the rigid section of the probe close to the imaging tip should be as short and as small in diameter as possible. Current ultrasound array probes used for these purposes are rigid over several millimeters, limiting their maneuverability.

Similarly, for improved flexibility, among other things, the number of electrical connections connecting the probe to the back end imaging system should also be limited. In other words, a larger number of cables make the catheter less flexible. The number of external connections is also important, for example, because excessive external connections increase probe size, manufacturing cost, and complexity.

In addition, to enable the probe to enter small areas (e.g., blood vessels), for example, the frontal area of the probe must be limited. To obtain the better resolution given the limited area of the probe, however, the transmit (Tx) and receive (Rx) array elements can be placed in sparse arrays around substantially the entire chip surface and can comprise integrated electronics for control. Furthermore, where possible, the Tx and Rx array elements should be separated and may further comprise dummy elements to achieve high signal to noise ratio with minimal cross-talk. In addition, phasing and other control features can enable ultrasound beam forming to enable the shape and/or direction of the ultrasound radiation to be altered for imaging purposes.

What is needed, therefore, is a single chip, flexible, forward-looking ultrasonic probe. The probe should comprise various optimized chip layouts. The probe should comprise improved resolution, reduced imaging time, reduced cross-talk, and improved beam direction and shaping. It is to such an ultrasonic probe that embodiments of the present invention are primarily directed.

SUMMARY OF THE INVENTION

Embodiments of the present invention relate to ultrasound imaging probes and particularly to forward-looking, energy-efficient ultrasound imaging probes with onboard electronics. Embodiments of the present invention can enable improved imaging with reduced sample times. Embodiments of the present invention can enable improved imaging with reduced sample times.

Embodiments of the present invention can comprise a CMUT on CMOS chip for imaging applications comprising a CMOS chip comprising a CMUT array. In some embodiments, the CMUT array can comprise a plurality of CMUT transmit ("Tx") elements, a plurality of CMUT receive ("Rx") elements, a plurality of dummy CMUT ("Cx") elements to reduce cross-talk between the plurality of CMUT transmit elements and the plurality of CMUT receive elements. In some embodiments, the Cx elements can comprise CMUT elements with collapsed diaphragms. In other embodiments, the Cx elements can comprise solid CMUT elements.

In some embodiments, the CMUT on CMOS chip can be connected to one or more outputs disposed proximate the back side of the chip with flex tape. In some embodiments, the flex tape can be routed through an aperture in the chip to the one or more outputs. In other embodiments, the flex tape can be routed around one or more locations on the periphery of the chip. In still other embodiments, the flex tape can be disposed such that it overlies at least a portion of the CMUT array.

In some embodiments, at least a portion of the plurality of CMUT Tx elements can be disposed in two or more concentric rings to form a defocused annular array. The chip can further comprise a protective layer disposed in an overlying manner to the CMUT array. In a preferred embodiment, the protective layer comprises a material with substantially the same acoustic impedance as blood.

Embodiments of the present invention can also comprise a CMUT on CMOS chip for imaging applications comprising a CMOS chip. In some embodiments, the CMOS chip can comprise a plurality of CMUT transmit ("Tx") elements and a plurality of CMUT receive ("Rx") elements. In a preferred embodiment, the Tx elements are disposed in a first, substantially hexagonal, array on the CMOS chip and the Rx elements are disposed in a second, substantially hexagonal, array on the CMOS chip. In another preferred embodiment, the number of CMUT elements in the first and second arrays is a multiple of 6.

In some embodiments, the first array can be disposed concentrically inside the second array. In other embodiments, the second array can be disposed concentrically inside the first array. In some embodiments, to increase transmission output power, two or more of the Tx elements in the first array can be batch fired. In some embodiments, at least a portion of the plurality of CMUT elements in the hexagonal Tx array can be disposed in two or more concentric rings to form a defocused annular array.

In a preferred embodiment, the first array comprises k central CMUT Tx elements and 6 k peripheral CMUT Tx elements, where k≥1 and an integer. In this manner, the peripheral CMUT Tx elements can be disposed in a substantially hexagonal array around the central CMUT Tx elements. In some embodiments, the central CMUT Tx elements can each comprise a central element electrode and the peripheral CMUT Tx elements can each comprise a peripheral element electrode. In this configuration, the central elements electrode (s) can be connected to a different circuit than the peripheral element electrode(s) to create a phase shift, a difference in amplitude, or both between the central CMUT Tx elements and the peripheral CMUT Tx elements. In a preferred embodiment, the central elements electrode(s) are larger than the peripheral element electrode(s).

In some embodiments, the Tx element electrodes each comprise dual electrodes. In other embodiments, the Tx element electrodes can be sized and shaped to substantially cover the Tx elements and the Rx elements electrodes can be sized and shaped to cover between approximately 50%-80% of the Rx elements.

Embodiments of the present invention can also comprise a CMUT on CMOS chip for imaging applications comprising a CMOS chip comprising a substantially hexagonal transmit ("Tx") array. In some embodiments, the Tx array can comprise a plurality of CMUT Tx subarrays arrays each subarray comprising a plurality of CMUT Tx elements disposed in a substantially hexagonal subarray and a substantially hexagonal receive ("Rx") array comprising a plurality of CMUT receive ("Rx") subarrays arrays each comprising a plurality of CMUT Rx elements disposed in a substantially hexagonal subarray. In some embodiments, one or more of the Tx subarrays further comprises a defocused annular subarray.

These and other objects, features and advantages of the present invention will become more apparent upon reading the following specification in conjunction with the accompanying drawing figures.

BRIEF DESCRIPTION OF THE FIGURES

FIGS. 14c-14f depict a PSF and a simulated images for arrays optimized using simulated annealing, in accordance with some embodiments of the present invention.

DETAILED DESCRIPTION

Figure 1B:
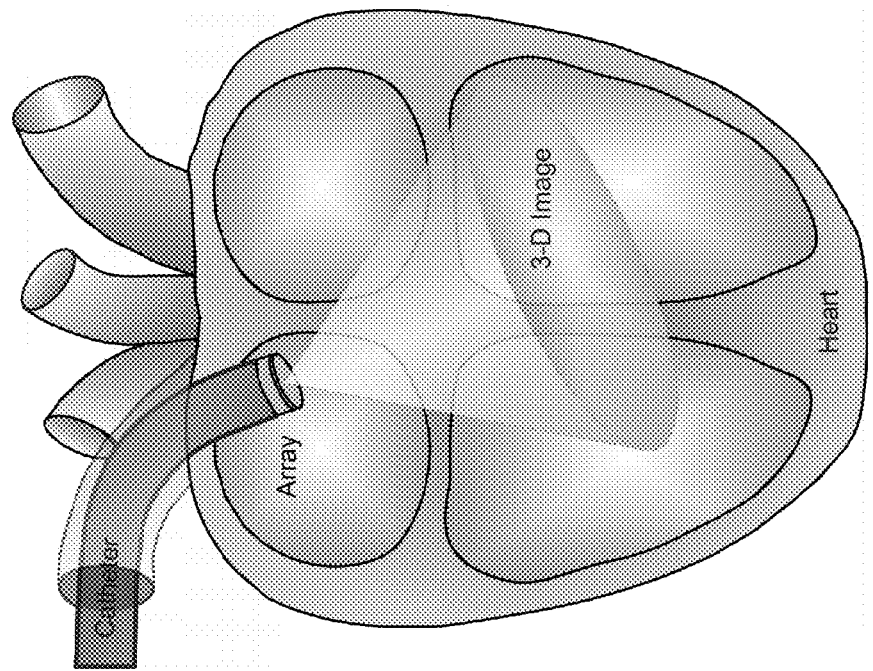
FIGS. 1a and 1b depict a forward-looking ultrasound catheter in use in a blood vessel and a heart, respectively, in accordance with some embodiments of the present invention.
Figure 1A:
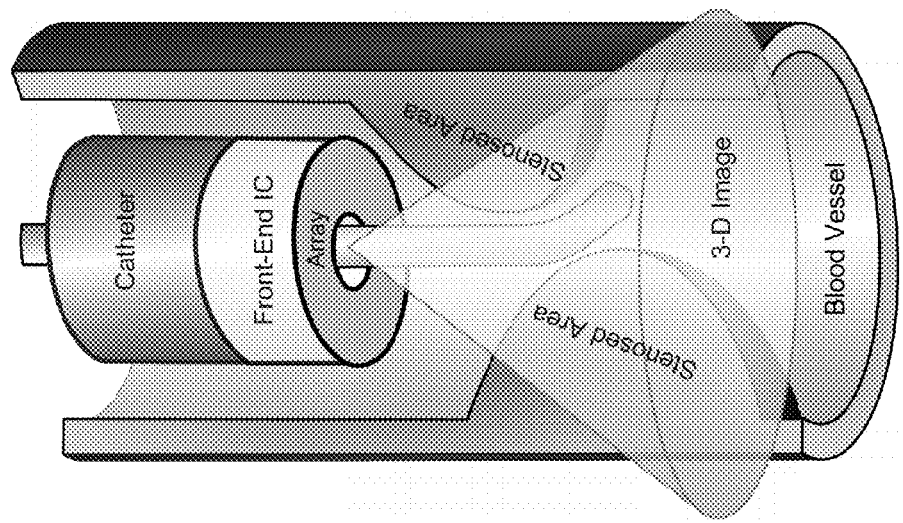

Embodiments of the present invention can comprise an ultrasound imaging probe with optimized electronics, intelligent control, and improved architecture. Embodiments of the present invention provide improved image resolution, reduced imaging times, or a combination thereof. Embodiments of the present invention can utilize a multi-faceted approach including, but not limited to, careful selection of probe architecture and connection methods, beam shaping, reduced cross-talk, and improved CMUT on CMOS architecture. To this end, CMUT on CMOS electronics can be devised to improve packaging, beam forming, and transmit power, while reducing energy consumption.

To simplify and clarify explanation, the system is described below as a system for intravascular ultrasound imaging. One skilled in the art will recognize, however, that the invention is not so limited. The system can also be deployed for other ultrasound imaging applications, particularly when a small catheter cross-section is desired. The system can also comprise an energy efficient, miniaturized chip for ultrasound imaging.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As mentioned above, for ultrasound imaging in the heart or blood vessels, e.g., for diagnostic and intervention guiding applications, it is desirable to have a catheter with a smallest possible diameter and rigid section so that the imaging device can be placed in the desired location in, for example, tortuous arteries or can be easily steered to provide an image in the desired direction. In other words, it is preferable for the catheter to contain a chip that is both small in diameter and thin. In this manner, the diameter of the catheter can be minimized while its flexibility is maximized.

To this end, CMUT based catheters comprising a single silicon substrate which contains both the CMOS electronics and CMUT ultrasound arrays can be built using CMUT-on-CMOS technology. These chips can be designed to require a small number of external electrical connections such as, for example and not limitation, between approximately 5 and 16 connections. In addition, these electrical connections, or ports, can be provided using a flexible connection means, such as, for example, flex-tape or flex circuits, further improving catheter flexibility. This combination can result in an array with a rigid cross-section smaller than 1 mm. The flexible interconnect tape can be connected from the front of the chip, back of the chip (e.g., using through vias), or at the sides.

In some embodiments, the chip can be thinned down to approximately 100 µm. In some embodiments, the chip can also be attached to a backing layer and/or a small rigid substrate to enable the necessary interconnects (e.g., a flex-tape to coax cable connection). In other embodiments, such as for use with an arterial guide wire, the chip can be substantially donut shaped to enable the wire, or other intervention tools, to pass through the center of the chip. In still other embodiments, the chip can be other suitable shapes, such as substantially disk shaped, depending on, for example and not limitation, whether a guide wire is used, where the guide wire is attached to the chip, and/or whether intervention devices are desired.

The CMUT transmit and receive ultrasound arrays can comprise, for example and not limitation, single or multiple rings, or sparse arrays with multiple frequencies and multiple transmit and receive functions. Various transmit and receive schemes and electronic control systems have been disclosed. See, U.S. patent application Ser. No. 13/412,465 entitled, "Compact, Energy-Efficient Ultrasound Imaging Process using CMUT Arrays with Integrated Electronics," by the inventor herein, filed 15 Mar. 2012, which is hereby incorporate by reference as if set forth in its entirety below.

Figure 2A:
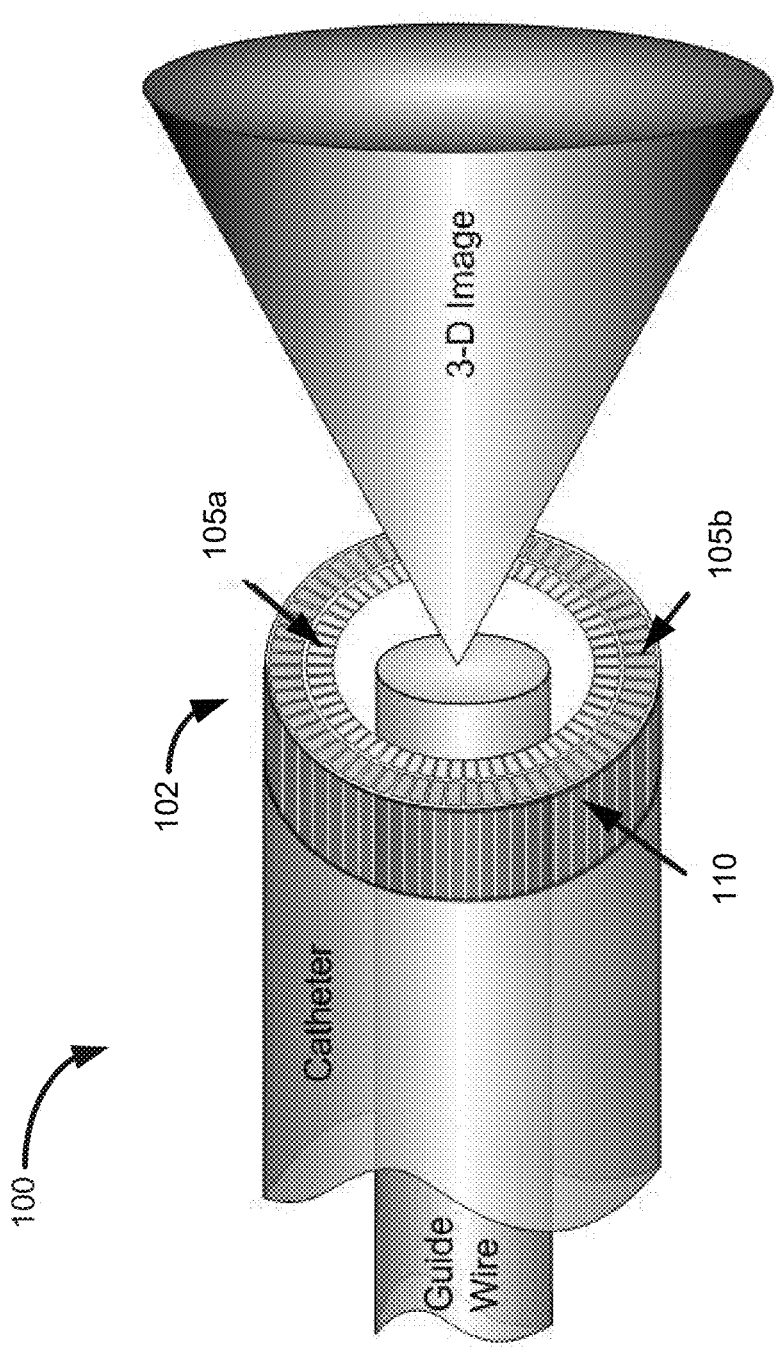
FIG. 2a depicts a forward-looking ultrasound imaging system, in accordance with some embodiments of the present invention.
Figure 2B:
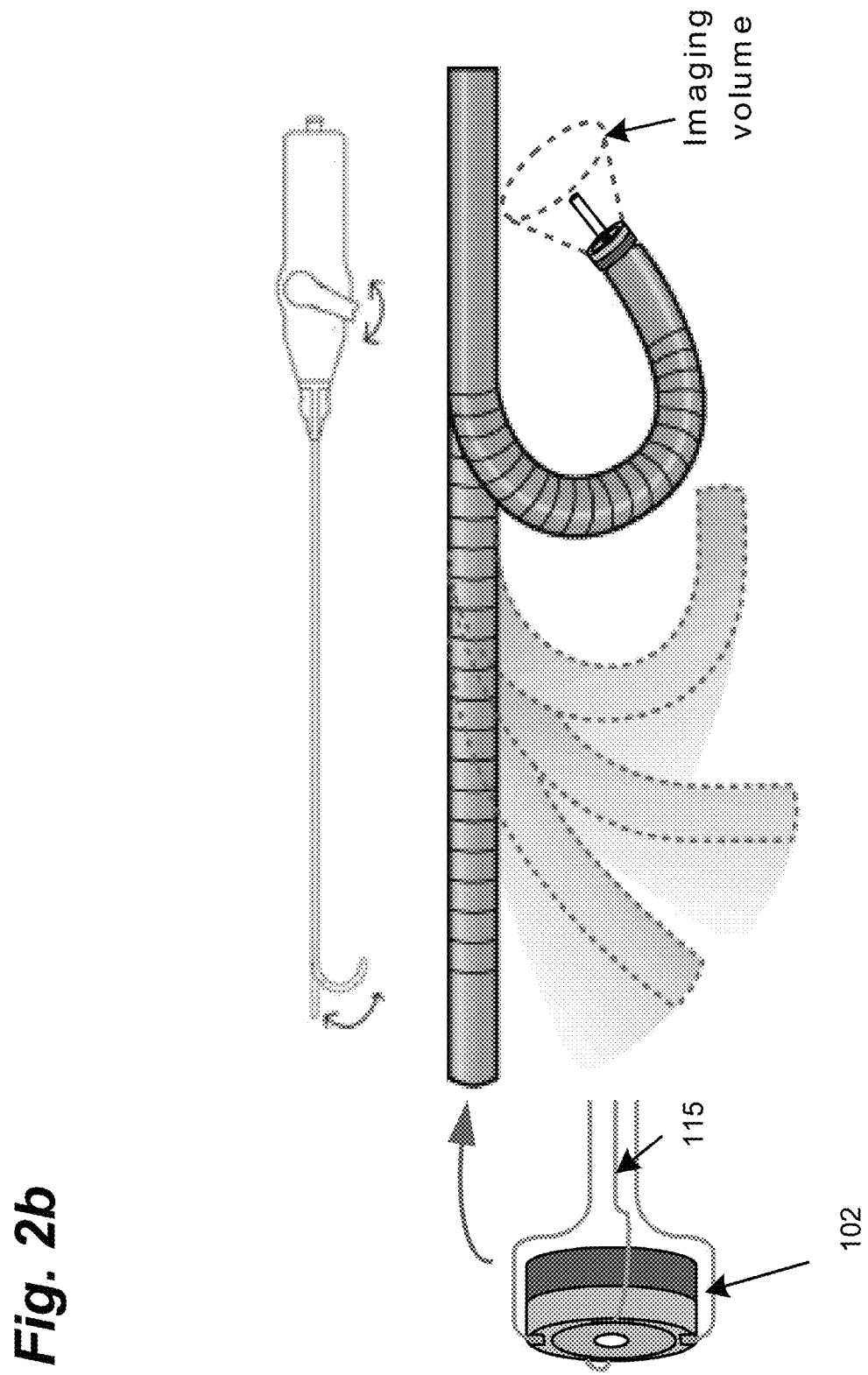
FIG. 2b depicts a forward-looking ultrasound probe, in accordance with some embodiments of the present invention.

As shown in FIGS. 2a and 2b, embodiments of the present invention can comprise a single chip CMUT-on-CMOS array 102 for use with a flexible ultrasound imaging probe 100. In some embodiments, a single chip 102 can contain a plurality of CMUT transmit (Tx) 105a and receive (Rx) 105b elements along with CMOS electronics 110 to provide the necessary controls. In some embodiments, the first level of connection (i.e., from the chip 102) can be done using, for example and not limitation, flexible interconnects (e.g., flex tape 115). In other embodiments, the chip 102 can comprise through vias to enable connection to the rear side of the chip.

Figure 3:
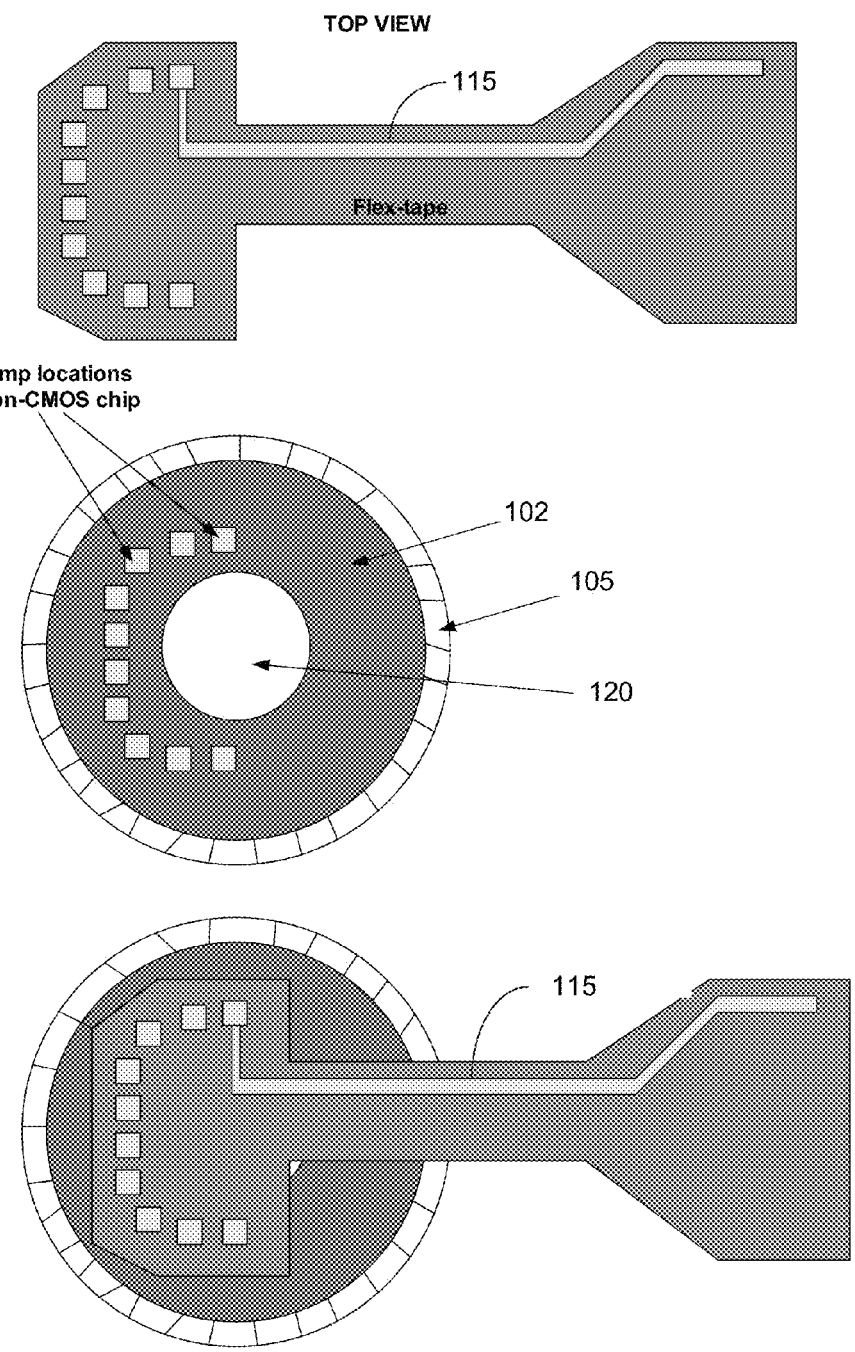
FIG. 3 depicts a forward-looking ultrasound catheter with external flex tape connections, in accordance with some embodiments of the present invention.

As shown in FIGS. 2b and 3, in some embodiments, flexible interconnects 115 can be used and can be connected proximate the outer periphery of the chip 102. The flex tape 115 can be folded, for example, around the outside of the chip 102 and below to additional external connections (e.g. coaxial cable connections). This may be desirable because, for example, a solid, disk-shaped chip 102 is used with no internal apertures 120. In other embodiments, chip apertures 120 may be otherwise occupied by, for example and not limitation, guide wires and intervention tools. Due to the minimal thickness of the flex tape 115 (e.g., approximately 5-10 µm), the increase in diameter of the chip 102 is relatively negligible, particularly for cardiac, or other large vessel, imaging.

Figure 4:
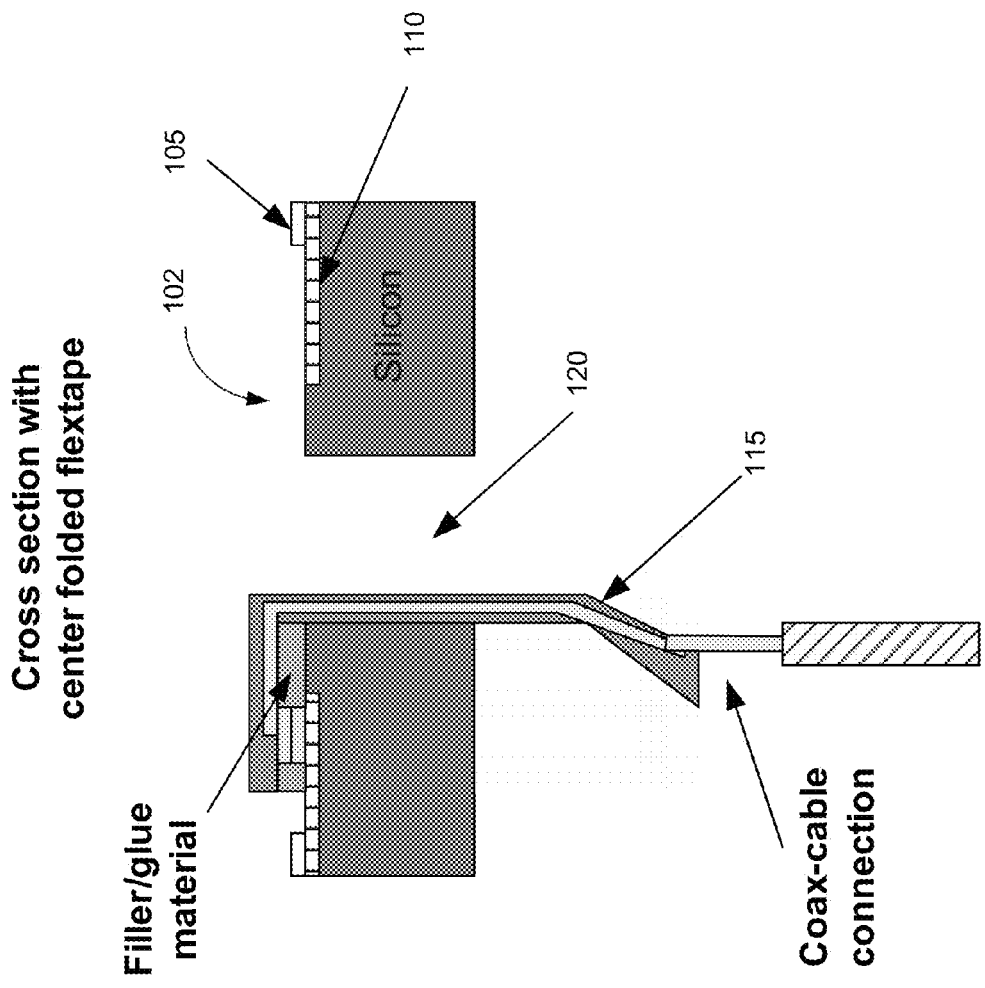
FIG. 4 depicts a forward-looking ultrasound catheter with internal flex tape connections, in accordance with some embodiments of the present invention.

For smaller vessel imaging, it may be necessary, however, to further reduce the diameter of the imaging probe 100. In other embodiments, therefore, as shown in FIG. 4, the flex tape 115 connections can be made through the center 120 of the chip 102. In some embodiments, for example, the flex tape 115 can be connected and folded into the opening 120 and through for connection below the chip 102. In this configuration, the overall cross-section of the chip 102 can be reduced. This configuration can also reduce the possible shadowing effect of the interconnect structure on the imaging beam generated by the CMUT array elements 105.

Figure 5:
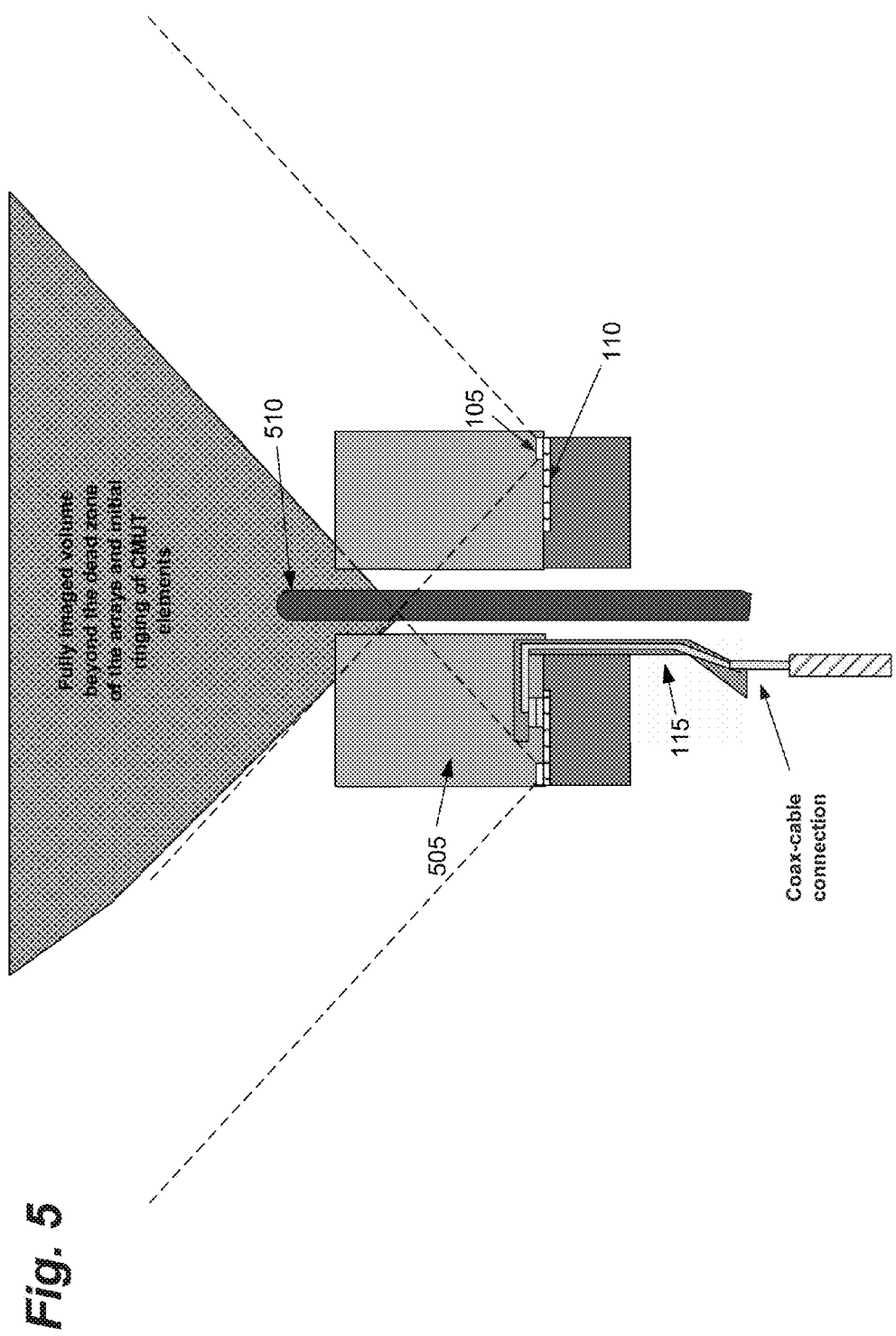
FIG. 5 depicts a forward-looking ultrasound catheter with internal flex tape connections and a protective cover, in accordance with some embodiments of the present invention.

As shown in FIG. 5, in some embodiments, the flex-tape 115 material, e.g. polymer or polyimide material, can be made thin (approximately 5-10 um) and the acoustic impedance can be matched closely to that of water and blood. In this configuration, the flex-tape 115 can cover substantially the entire surface of the chip 102 without affecting imaging. In some embodiments, the flex tape 115 can be sandwiched between a protective fluid-like layer 505 such as, for example and not limitation, polydimethylsiloxane (PDMS), which also can have substantially the same acoustic impedance as blood. The protective layer 505 can protect the face of the chip 102 and the flex tape 115 to prevent damage, for example, as the chip 102 is guided through, and contacts vessel walls or other internal bodily structures. In some embodiments, as shown, the protective layer 505 can be approximately 1 mm thick to enable the guide-wire 510, or intervention tool, to be seen in the image outside the blind region of the array 105.

Hexagonal Array

Figure 6:
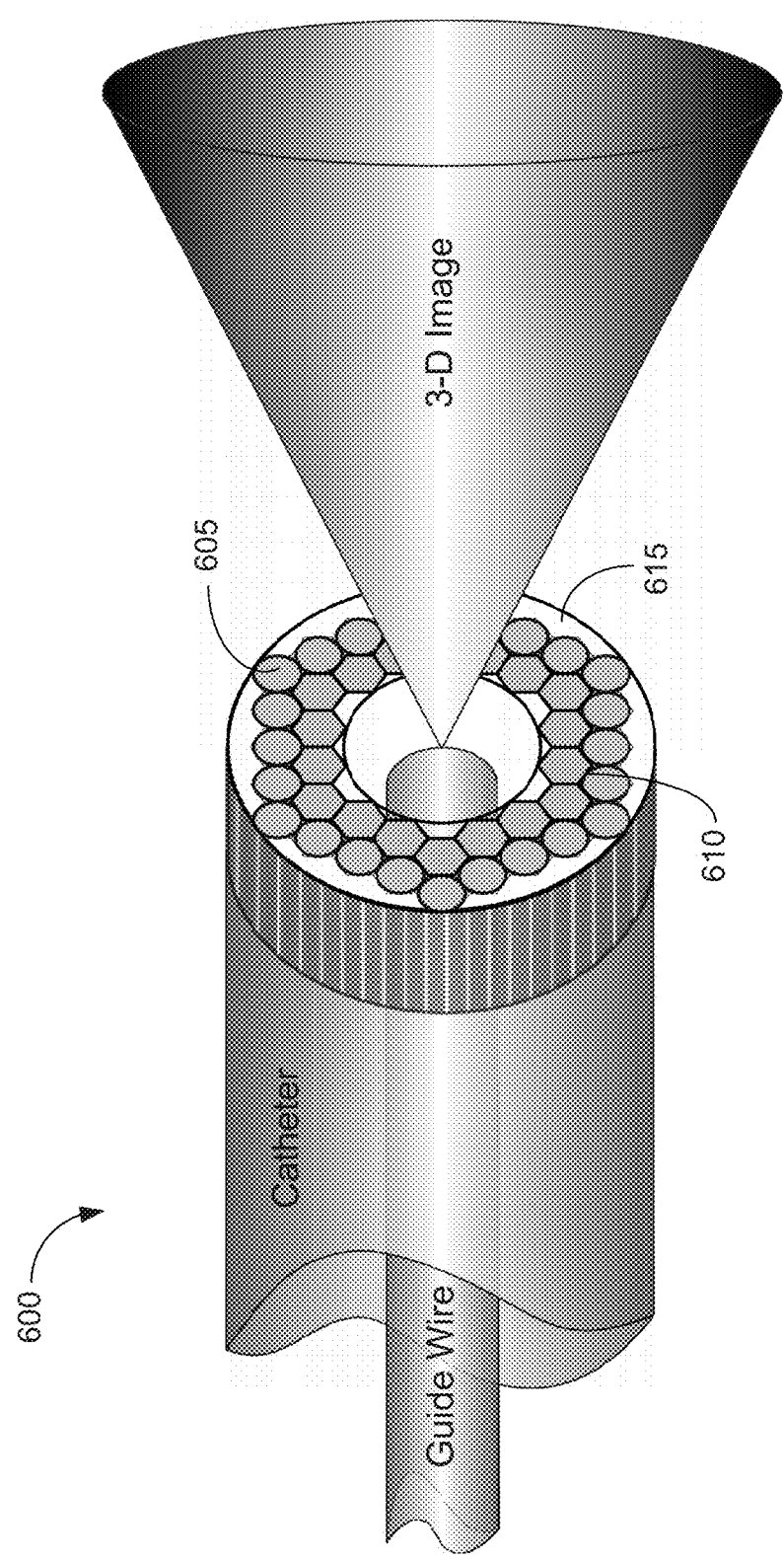
FIG. 6 depicts a forward-looking ultrasound catheter comprising a hexagonal array, in accordance with some embodiments of the present invention.
Figure 7:
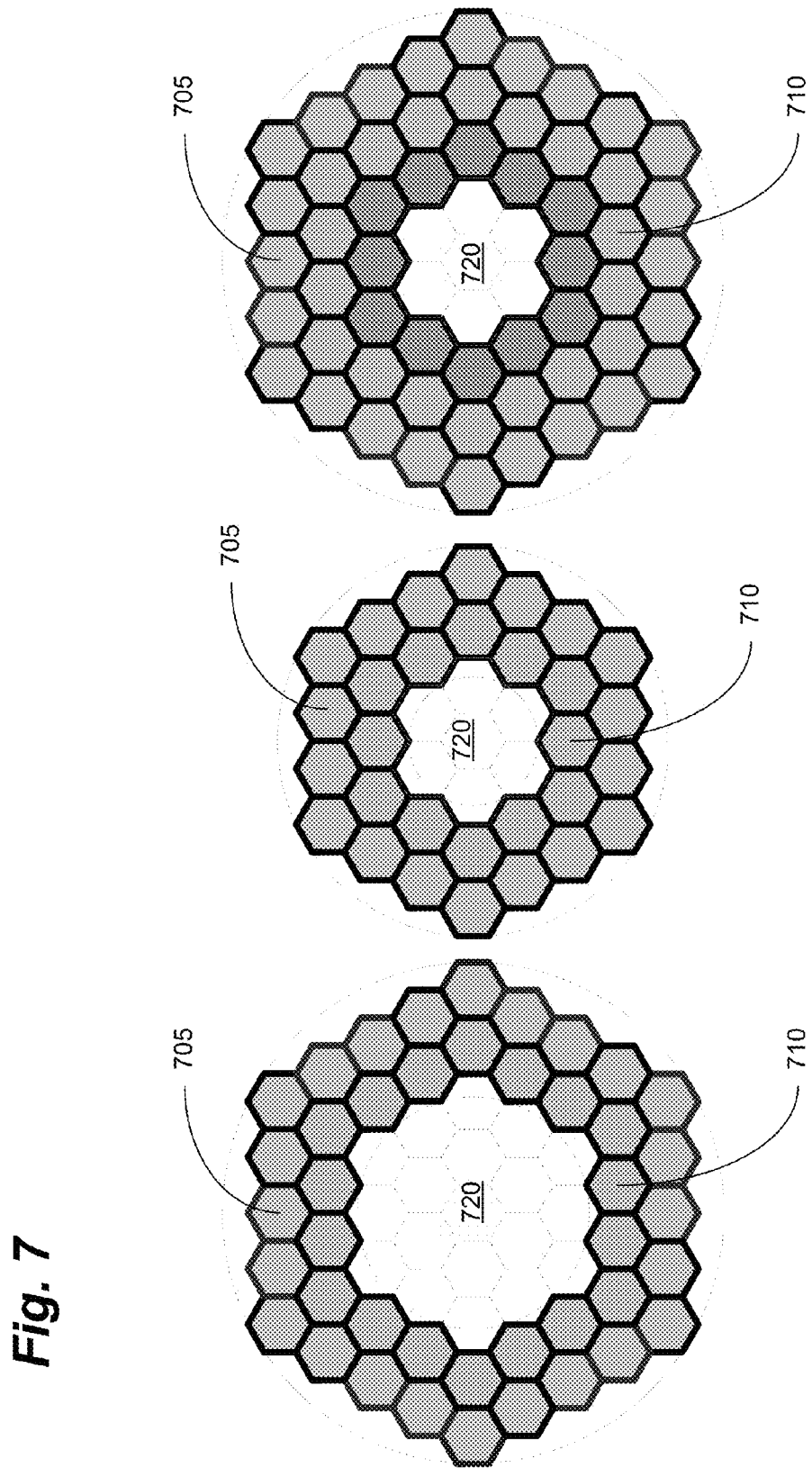
FIG. 7 depicts various embodiments of a hexagonal array, in accordance with some embodiments of the present invention.

As shown in FIG. 6, embodiments of the present invention can also comprise a dual hexagonal ring array 600. In some embodiments, the hexagonal design can be based on a hexagonal sampling, where a subset of each Tx 605 and Rx 610 subarrays can form a complete uniformly filled hexagonal coarray 600 without any redundancy in spatial frequencies. This geometry can provide a large coarray 600 with a reduced number of firing events. This can be achieved, for example, by filling the spatial frequency space uniformly, but with small number of firings. In a preferred embodiment, therefore, the available surface area on the CMUT array surface 615 can be divided into hexagonal shapes which can, in turn, be filled with subarrays 605, 610 (i.e., a group of CMUT elements). As shown in FIG. 7, different array configurations with different ring and element 705, 710 counts and aperture sizes 720 can be formed to meet a variety of imaging needs.

Figure 8:
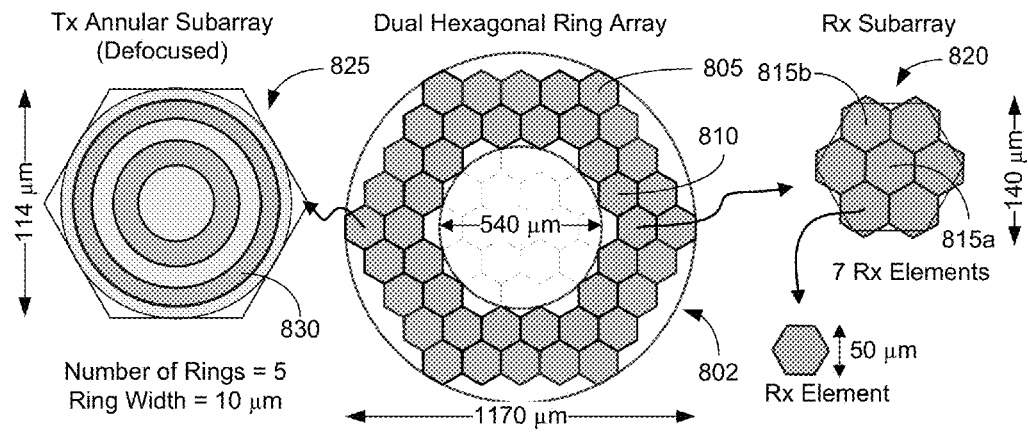
FIGS. 8-9 depict additional hexagonal arrays, in accordance with some embodiments of the present invention.
Figure 9:
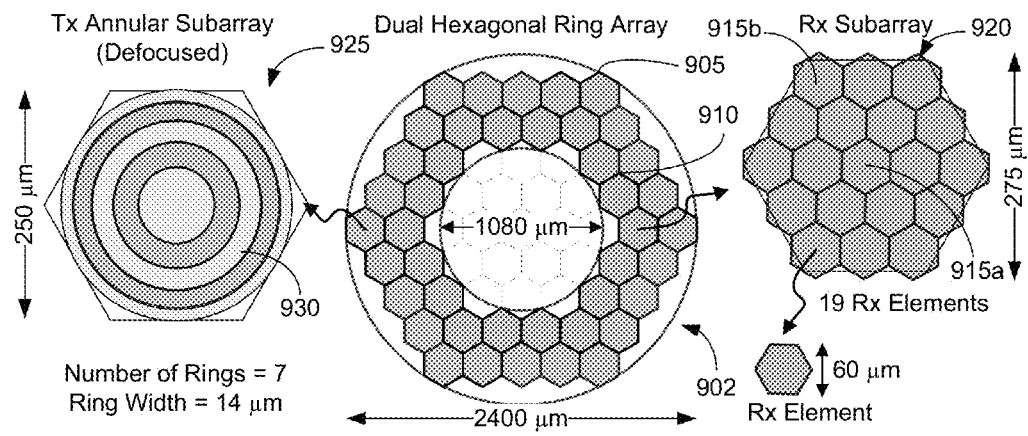

In some embodiments, as shown in FIGS. 8 and 9, each of the hexagonal areas 805, 810 can be subdivided into different CMUT elements 815. On the receiver subarray 820, for example, the hexagonal subarray 820 can comprise 7 individual CMUTs 815 comprising a central CMUT 815a, surrounded by a hexagonal array of 6 CMUTs 815b. Due to the integration provided by CMOS technology, each of these small CMUTs 815 can be connected to a receiver amplifier integrated on the same silicon chip 802. The outputs of these amplifiers can then be multiplexed using a digital controller and output from the chip 802 using an electrical interconnect. The number of CMUT elements 815 filling the hexagon can change depending on available area and electronics channels. In FIG. 9, for example, each receiving hexagonal sub array 920 is filled with 19 CMUT elements 915. In a preferred embodiment, the size of the individual CMUT elements 915 in the hexagonal subarray 920 is smaller than the wavelength of the ultrasonic waves at the frequency of operation.

In some embodiments, the hexagonal arrays 820, 920 can employ a defocused annular subarray 825, 925 to emulate a powerful, virtual point-like source, capable of uniformly isonifying substantially the entire image volume. In some embodiments, the defocused annular array 825, 925 can comprise a small number of annular Tx array elements 830, 930 and can generate a circular, symmetric radiation pattern. As shown in FIGS. 8 and 9, for example, a single element 805, 905 from the dual hexagonal array 802, 902, can comprise an annular array 825, 925. The annular array 825, 925 can be made, for example, by having circular rings 830, 930 of membranes, which can then be phased to generate a spherical wave front. Of course, phasing can be used to create other wave front shapes such as, for example and not limitation, point sources, beams, and steered beams.

The hexagonal ring array 802, 902 configuration can provide a scalable design for different array specifications such as, for example and not limitation, available aperture size, number of subarray elements 815, 915 (e.g., channels), firing count, and element 815, 915 size. In a preferred embodiment, the number of subarrays 820, 920 on each hexagonal ring is a multiple of 6. In other words, the number elements 815, 915 in each subarray 820, 920 can be chosen as (1+6 k) where k>=1, an integer.

FIGS. 8 and 9 depict schematics of two particular hexagonal dual ring array designs suitable for FL-NUS and FL-ICE imaging. The outer 805, 905 and inner 810, 910 hexagonal rings can generate a coarray 802, 902 with a size equal to the sum of the ring sizes. See, e.g., Hoctor, R. T. and Kassam, S. A., The unifying role of the coarray in aperture synthesis for coherent and incoherent imaging, Proceedings of the IEEE, vol. 78, no. 4, pp. 735-752, 1990 (hereinafter, "Hoctor"). In some embodiments, a uniformly filled hexagonal coarray (e.g., non-redundant coarray) can be generated using a subset of Tx and Rx element combinations.

Figure 10:
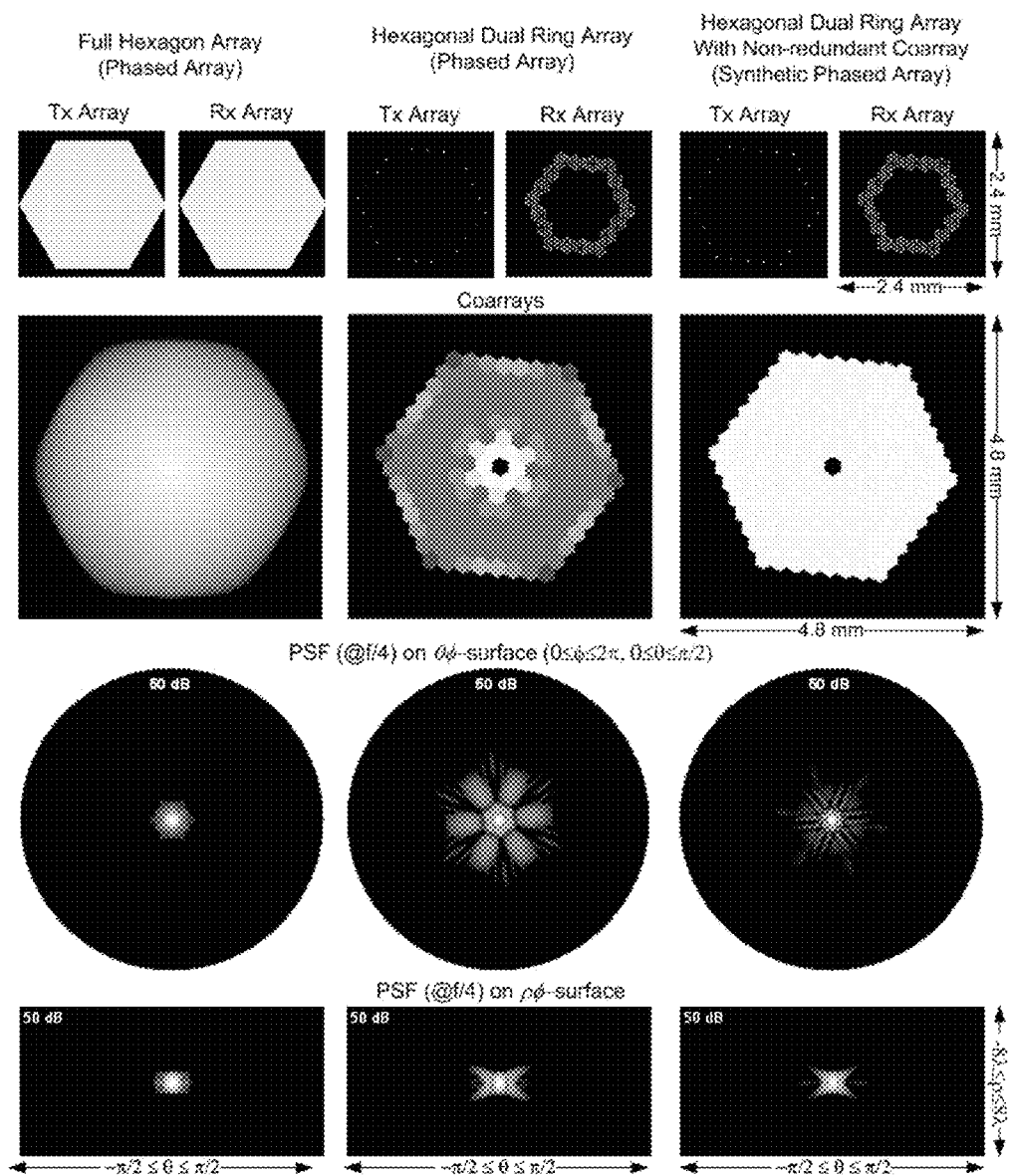
FIG. 10 depicts a comparison between images created by a full hexagonal array, a phased hexagonal array, and a synthetically phased hexagonal array, in accordance with some embodiments of the present invention.
Figure 11A:
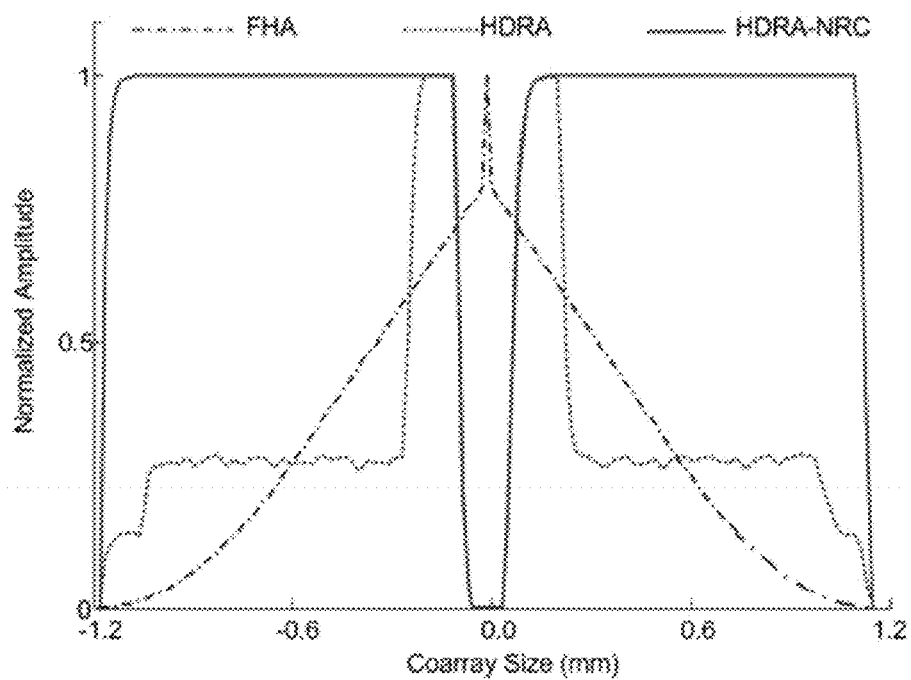
FIGS. 11a-11b compares the beam quality between a full hexagonal array and a non-redundant coarray, in accordance with some embodiments of the present invention.
Figure 11B:
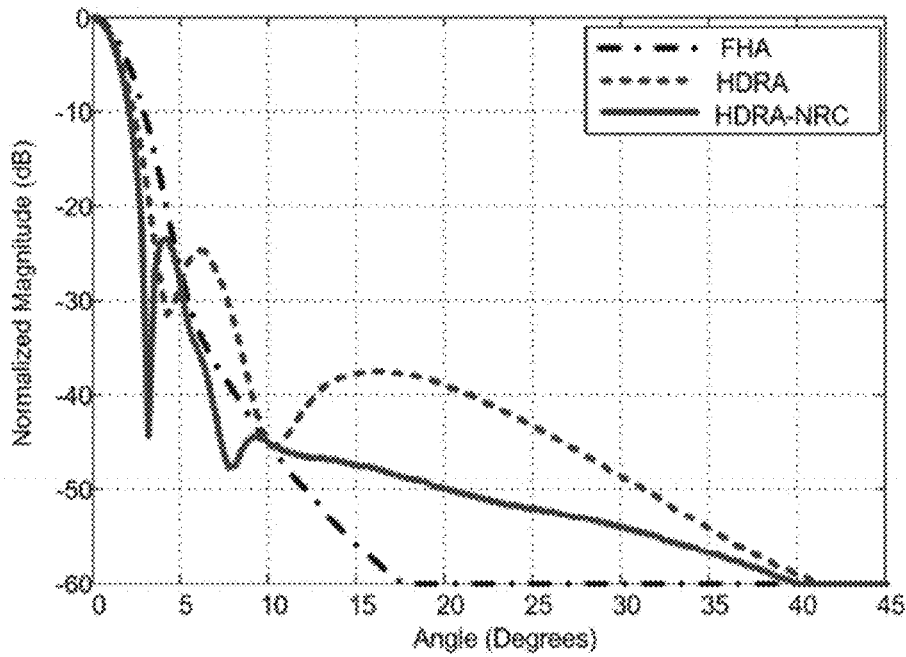

To have symmetric beam pattern, for example, the subset can be chosen in such a way that the number of elements 815, 915 in each subarray 820, 920 is substantially equal. Although the transmit 805, 905 and receive 810, 910 rings can generally be freely interchanged without altering the coarray 820, 920, the small subarray 820, 920 count on the inner ring 810, 910 can be more suitable for the receive operation, due to reduced receive channel complexity. Because the overall coarray size is the sum of the size of the Tx 805, 905 and Rx 810, 910 arrays, the hexagonal array 802, 902 design can enable forming non-redundant coarrays, where each coarray element 815, 915 can be independently controlled in terms of the spatial location and element weighting. This allows one to form any desired beam pattern To demonstrate the imaging performance of the proposed array structure, FIG. 10 depicts a simulation of a particular hexagonal dual ring array with 2.4-mm outer diameter and 10 MHz center frequency and 50% fractional bandwidth for use with a 2.6-mm diameter ICE catheter. The simulated point spread functions ("PSF"s) are presented in FIGS. 10, 11a, and 11b. As shown, the hexagonal dual ring array with non-redundant coarrays generate beam quality substantially similar to the full hexagon array.

Sparse Arrays

Despite being limited by the relatively small-size of an IVUS imaging catheter, for example, image quality and sampling times are largely dependent on the number of Tx-Rx pairs available and the area occupied thereby. In other words, Tx-Rx arrays spaced over the entire chip, as opposed to rings or clusters that occupy only part of the chip, can provide improved image quality even at lower resolutions (i.e., firing events). In this manner, the CMUT-on-CMOS architecture with improved electronics disclosed herein enables, among other things, improved image resolution and/or reduced sampling times.

Figure 12:
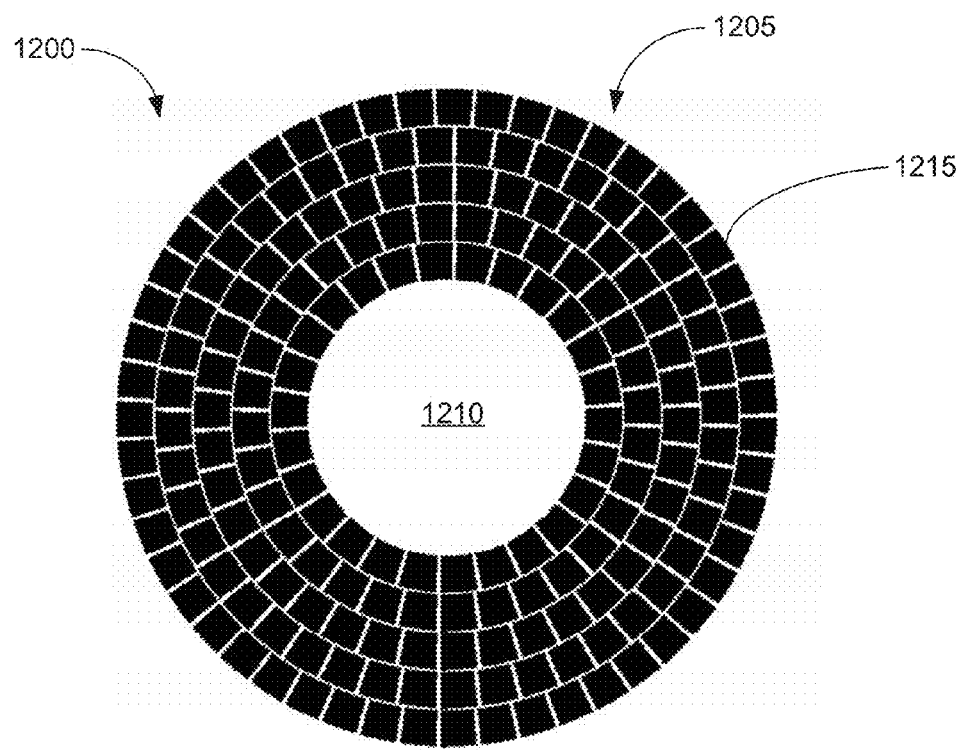
FIG. 12 depicts a multi-ring transmit (Tx) and receive (Rx) array for use with a forward-looking ultrasound catheter, in accordance with some embodiments of the present invention.

Embodiments of the present invention enable this improved functionality in several ways. As shown in FIG. 12a, for example, the CMUT-on-CMOS approach can enable the use of the whole available silicon chip area 1200, for example, to place arrays with nearly arbitrary element distribution. In addition, integrated electronics can enable addressing a large number of elements and multiple receive channels enabling faster data acquisition and/or synthetic aperture beamforming, among other things. The microfabrication processes disclosed herein also enable CMUT structures to be separately optimized for Tx and Rx operation on the same silicon chip 1200.

These features, in turn, can be exploited in a variety of ways. Using sparse array and co-array concepts along with optimization techniques, for example, array elements can be distributed over substantially the entire silicon area 1200 to improve image contrast and/or resolution while increasing the frame rate by reducing the number of firings and using multiple active receive channels. In other words, the image quality can be improved simply by increasing the area, or "spread," of the Tx-Rx arrays, instead of simply increasing the number of Tx-Rx arrays. This configuration can also enable the unused silicon areas created by the use of sparse array elements to implement mechanical structures, or "blanks," to reduce acoustical cross talk, further improving array performance.

Finally, the power limitations that may be introduced by the sparse CMUT Tx array elements can be overcome by forming groups, or sub-arrays, of Tx components. In this manner, multiple Tx elements can be fired simultaneously, or phased, to increase overall transmit power. These subarrays can, in turn, be phased using bias voltages and/or electrode shapes, while still using a separate Rx array with properly sized elements to increase signal-to-noise ratio ("SNR") and imaging depth. This can also enable beamforming to control the shape and/or direction of the imaging ultrasound beam for improved imaging.

Example 1

An example of the type of arrays that can be built using the CMUT technology is schematically shown in FIG. 12a. As shown, five annular rings 1205 can be formed with regular periodicity on a donut shaped silicon region 1200. This configuration is practical for an IVUS probe with a center opening 1210 for a guide wire or intervention tools, for example. Since it would be difficult, if not impossible, to both implement the front end electronics required for a phased array on this silicon chip 1200 and to provide the number of required external electrical connections to take full advantage of all the Tx and Rx elements 1215, in a preferred embodiment, synthetic array processing can be used.

Numerical modeling tools based on diffraction calculations or available software programs like FIELD-H can be used to evaluate the beam pattern quality and the PSF for a given firing set. In addition, co-array concepts such as those described in Hoctor can be used to obtain non-redundant Tx-Rx sets for dual-ring arrays to reduce the number of firings required to produce sufficient image quality. This can be done, for example, by choosing particular Tx and Rx combinations to uniformly fill the available coarray space, while eliminating redundant combinations that do not significantly improve the resolution (e.g., because the information is already contained in another combination). By eliminating redundant combinations, substantially the same image resolution can be obtained with significantly fewer transmit events (i.e., Tx 1215 firings). The reduced number of firings, in turn, reduces the time for data collection and computation time and hence can enable, for example, real-time imaging using synthetic arrays.

Figure 13A:
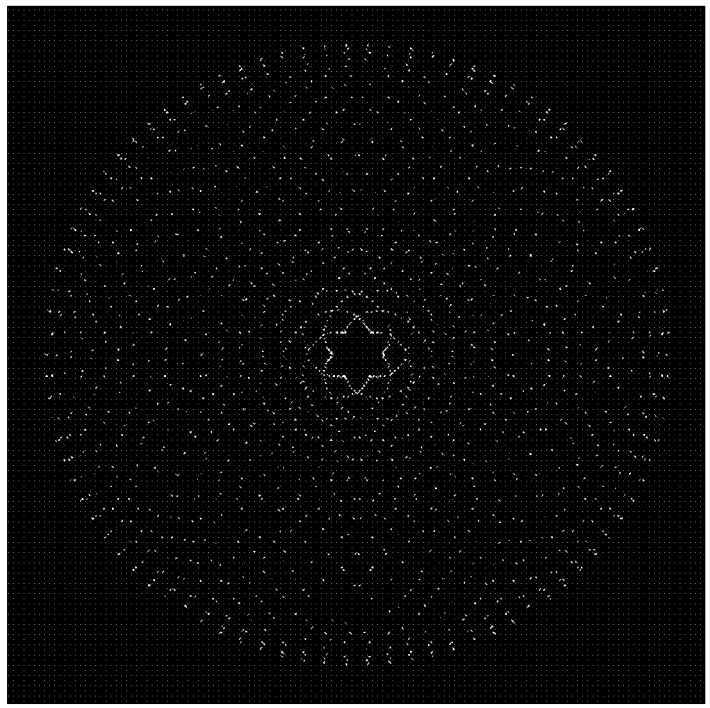
FIGS. 13a and 13b depict a point spread function (PSF) and a simulated image, respectively, for a full set of firings, in accordance with some embodiments of the present invention.
Figure 13B:
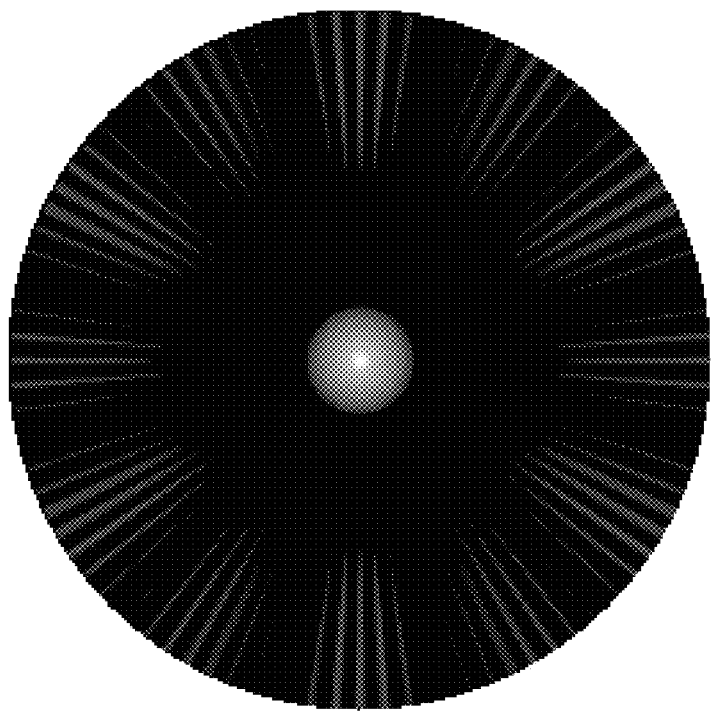
Figure 14A:
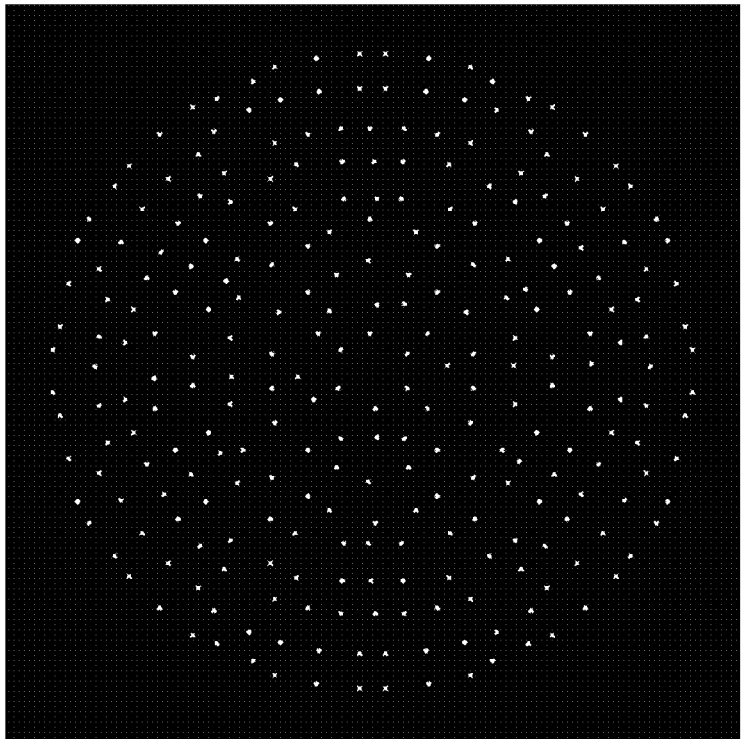
FIGS. 14a and 14b depict a PSF and a simulated image for a set of 256 non-redundant firings, in accordance with some embodiments of the present invention.
Figure 14B:
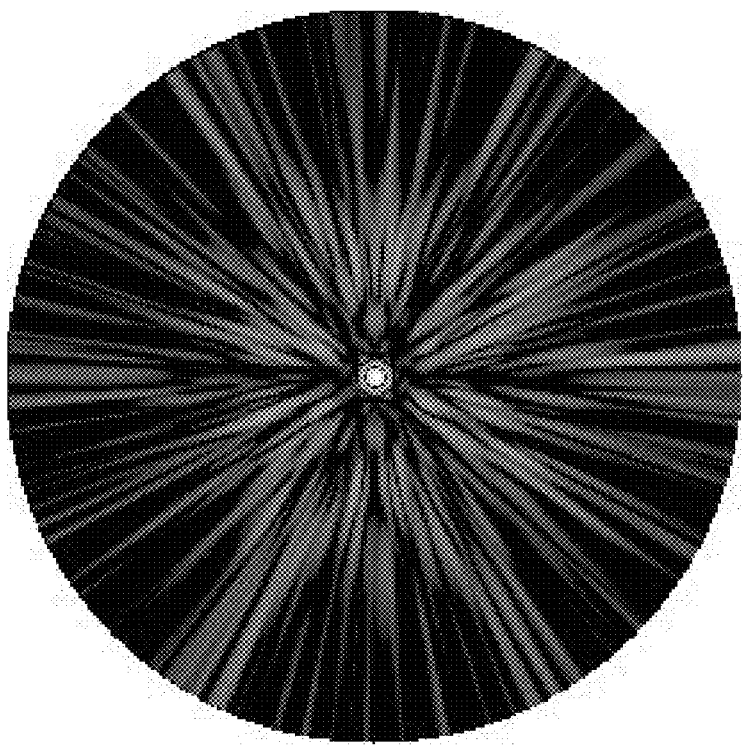

FIGS. 13a-14b depict an IVUS array with 48 Tx elements and 42 Rx elements. FIGS. 13a and 13b depict the co-array and corresponding PSF, respectively, for a full set of 2016 firings (i.e., each Tx element fired and received by each Rx element). FIGS. 14a and 14b, on the other hand, depict the same array, but utilizing a non-redundant set of 256 firings. As shown, the non-redundant set uses approximately 25 percent of Tx-Rx combinations, while producing substantially equivalent image quality within a 40 dB dynamic range. In addition, using the whole silicon surface 1200, as in FIG. 12a, provides additional freedom in choosing the Tx-Rx combinations to achieve the desired beam pattern performance when compared to, for example, single or dual ring annular arrays.

In some embodiments, for both sparse arrays and hexagonal ring arrays, the non-redundant firing sets can be obtained using optimization techniques such as simulated annealing. See, e.g., Murino, A. T., and C. S. Regazzoni, Synthesis of Unequally Spaced Arrays by Simulated Annealing, IEEE Trans. Signal Processing, 1996, 44, p. 119-123; see, also, An example of this optimization technique is given in the paper "Simulated annealing based optimization of dual-ring arrays for forward-looking IVUS and ICE imaging," Tekes, C.; Karaman, M.; Degertekin, F. L., 2010 IEEE Ultrasonics Symposium, Page(s): 999-1002.

To obtain a coarray pattern with a desired PSF performance the whole element subsets of the full set coarray can be searched. Generally, the problem cannot be solved by polynomial time as it is a non-deterministic polynomial time (NP-complete) problem. As a result, algorithms that can find near optimal solutions in reasonable time have become attractive. A simulated annealing algorithm, for example, can provide good optimization with reasonable computational costs. The Point Spread Function, H(.), is essentially the beam-formed pulse echo response of the array for each point in the space. It can be calculated for a point target using the Rayleigh-Sommerfeld diffraction formula using the following expression:

$$H(r, \theta, \varphi) = \sum_i w_i \cdot \sum_j w_j \cdot s\left(\frac{2r}{c} - t_i - t_j - \tau_i - \tau_j\right)$$

where $(r,\theta,\phi)$ are the spherical coordinates; i and j represent the Tx and Rx indices respectively; s(.) is the excitation pulse; c is the speed of sound; $t_i$ and $t_j$ are the flight times between the point target and Tx and Rx elements respectively; and $\tau_i$ and $\tau_j$ are the corresponding focusing delay times. The terms $w_i$ and $w_j$ represent the weighting coefficients. For simplicity, weighting can be used, such that each $w_{i,j}$ is unity. To avoid additional computational complexity, the element factor, obliquity factor, and attenuation effects can be ignored. The initial step for the optimization algorithm can be to calculate the PSF, including all the Tx-Rx firing combinations for all the sampled azimuth and elevation angles. This data can then be recorded for further use in the iteration steps to prevent repeating PSF calculations in each perturbation state. To find an optimum solution set from the full set coarray with a desired number of elements, therefore, an energy function can be defined that minimizes the peak side lobe level.

Example 2

To test the imaging performance of the optimized array configurations with dual circular and hexagonal ring arrays, custom numerical simulations can be performed assuming a dual-ring array of 64 Tx and 58 Rx elements. The diameters of the Tx and Rx arrays of the dual-ring array are assumed to be 1200 µm and 1080 µm, respectively. In this case, a hexagonal dual-ring array with 12, 7-element Rx subarrays and 28 Tx subarrays was used. The dual-ring circular array has 64 Tx and 58 Rx elements.

The effectiveness of the coarray patterns of 256 and 512 firings can be compared to a full set coarray of the corresponding array configurations, i.e., 3712 firing combinations (64×58=3712). Uniformly sampled coarrays can be obtained using a nearest neighbor technique and the coarrays can be optimized using simulated annealing, as discussed above. In this example, 400 iterations and 4000 perturbations can be used to obtain an optimized set. To obtain a circularly symmetric coarray and PSF distribution, a quarter of the coarray space can be used and then the solution can be extended to the other quarters symmetrically. This also results in symmetric Tx-Rx firing pairs. Additionally, this method performs the optimization on a relatively small search space, which reduces the computational time required to reach an optimum solution.

Figure 14C:
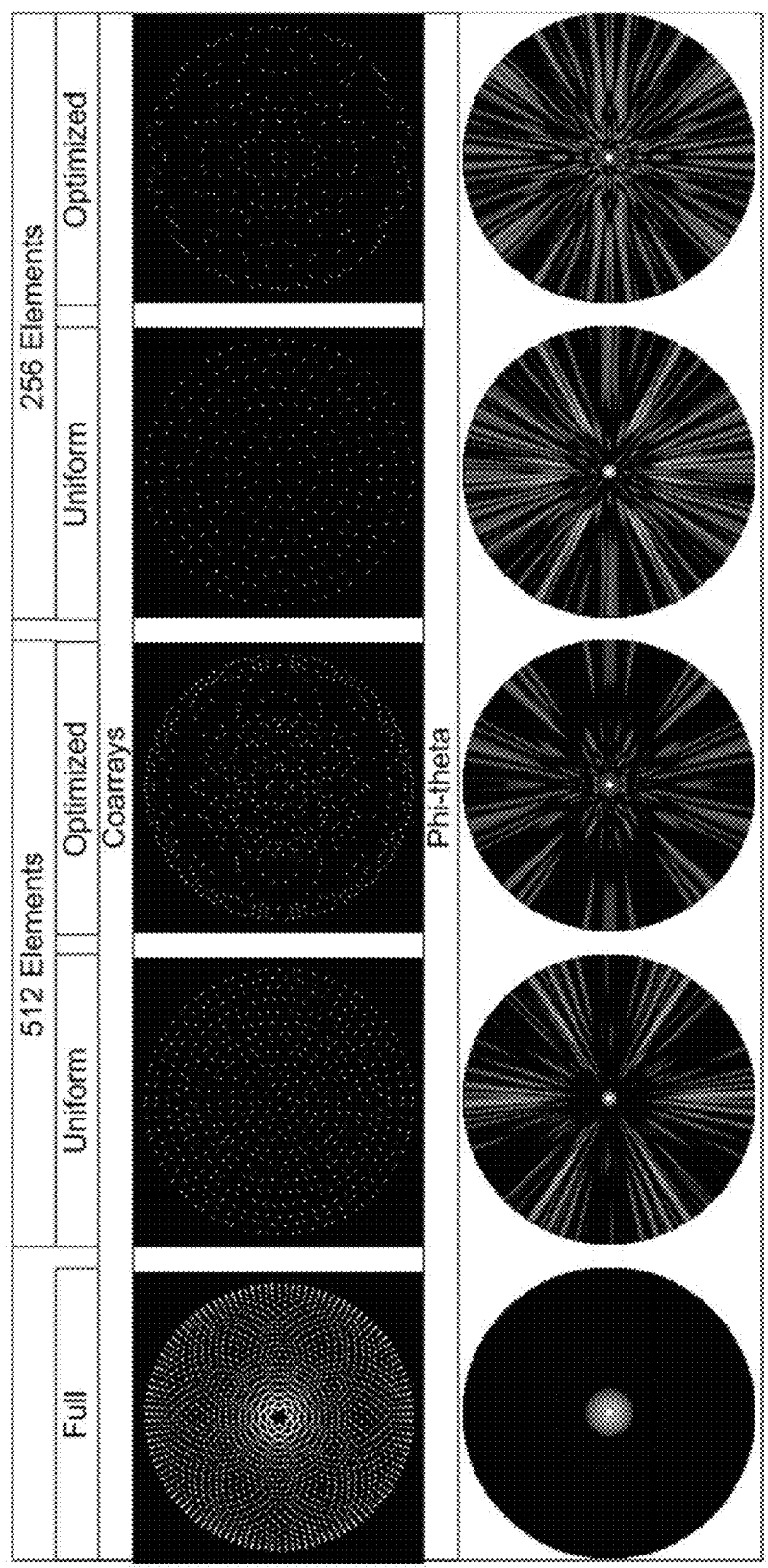

The coarrays produced by all the Tx-Rx element pairs (i.e., the full set), uniform sampled subarrays, and optimized subarrays are shown in FIG. 14c. For the wide-band PSF simulations of dual-ring array, the Gaussian pulse was set to a center frequency of 20 MHz, the speed of sound was 1540 m/s, and the fractional bandwidth was 50%. For this example, the target is located on the normal of the array (i.e., on the axis of the array) at F-number 4, i.e. at a distance 4 times the diameter of the array. As a result, the 2-D PSFs in FIG. 14c represent non-steered beam patterns.

Averaged 1-D lateral cross-sections of the PSFs are shown in FIG. 14d. As shown, the optimized coarray configuration has a narrow −6 dB main lobe width when compared with uniformly sampled and full set cases. For the first side lobe level, for example, the optimized coarray produces a nearly 10 dB reduction compared to the uniformly sampled and full sets. And, although the average side lobe level of uniformly sampled coarray decreases under the −40 dB level at approximately 10°, a relative rise at approximately −35 dB, in the far side lobe region, is also observed. In contrast, for the optimized coarrays in both the 512 and 256 element cases, there is a significantly flat side lobe level near −40 dB.

Figure 14E:
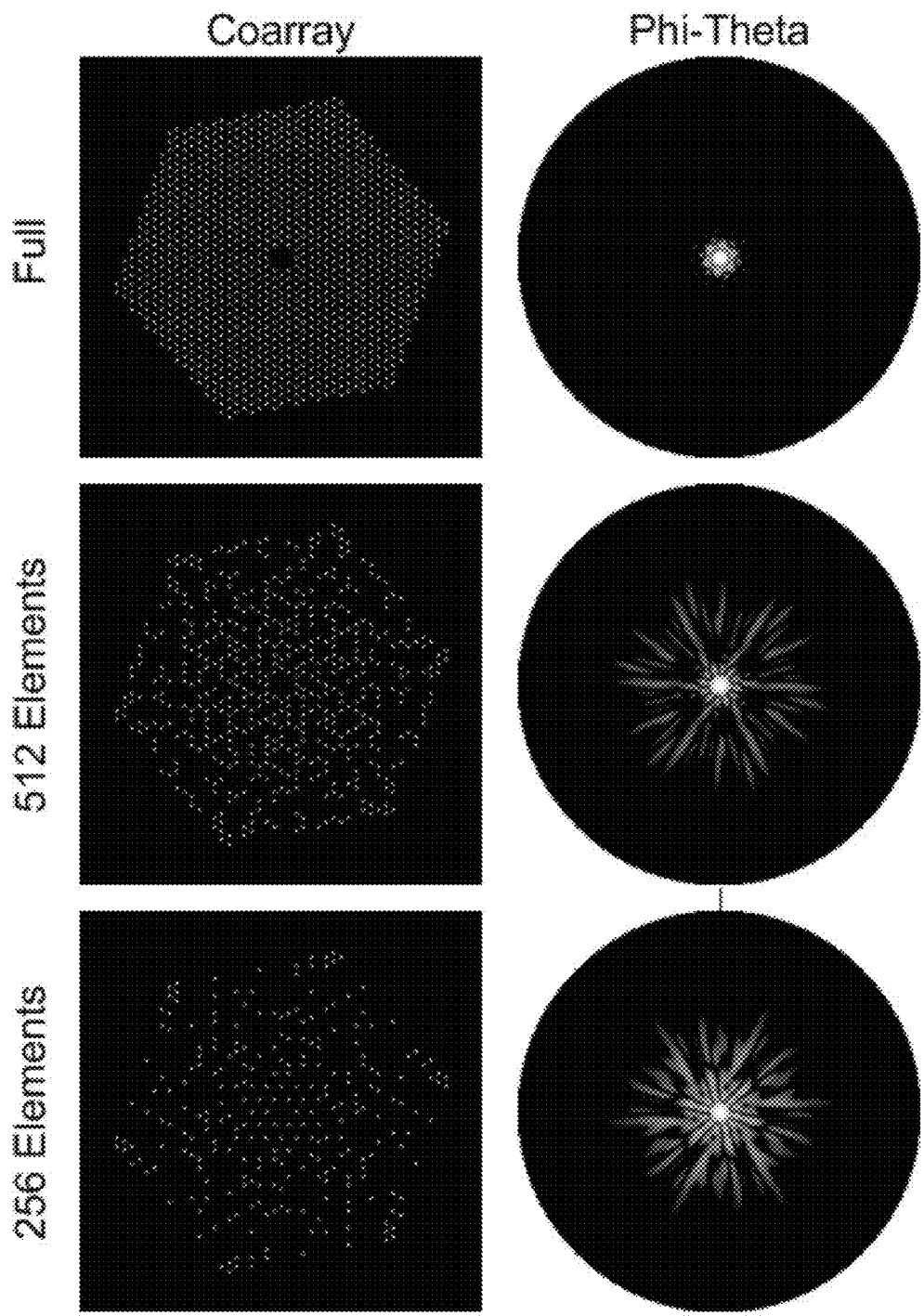

The subarrays in the dual hexagonal array can also be reduced and optimized using a simulated annealing optimization technique. The optimization results in this case are obtained for 258 and 516 element cases, as opposed to the as the full 1176 elements set (i.e., with redundancies eliminated from the full set). In the simulation 400 iterations and 2000 perturbations were used to obtain an optimized set. Similar to above, to obtain a circularly symmetric coarray and reduce the search space, elements from one sixth of the coarray space can be chosen and extended symmetrically. These results from these coarrays are shown in FIG. 14e.

Figure 14F:
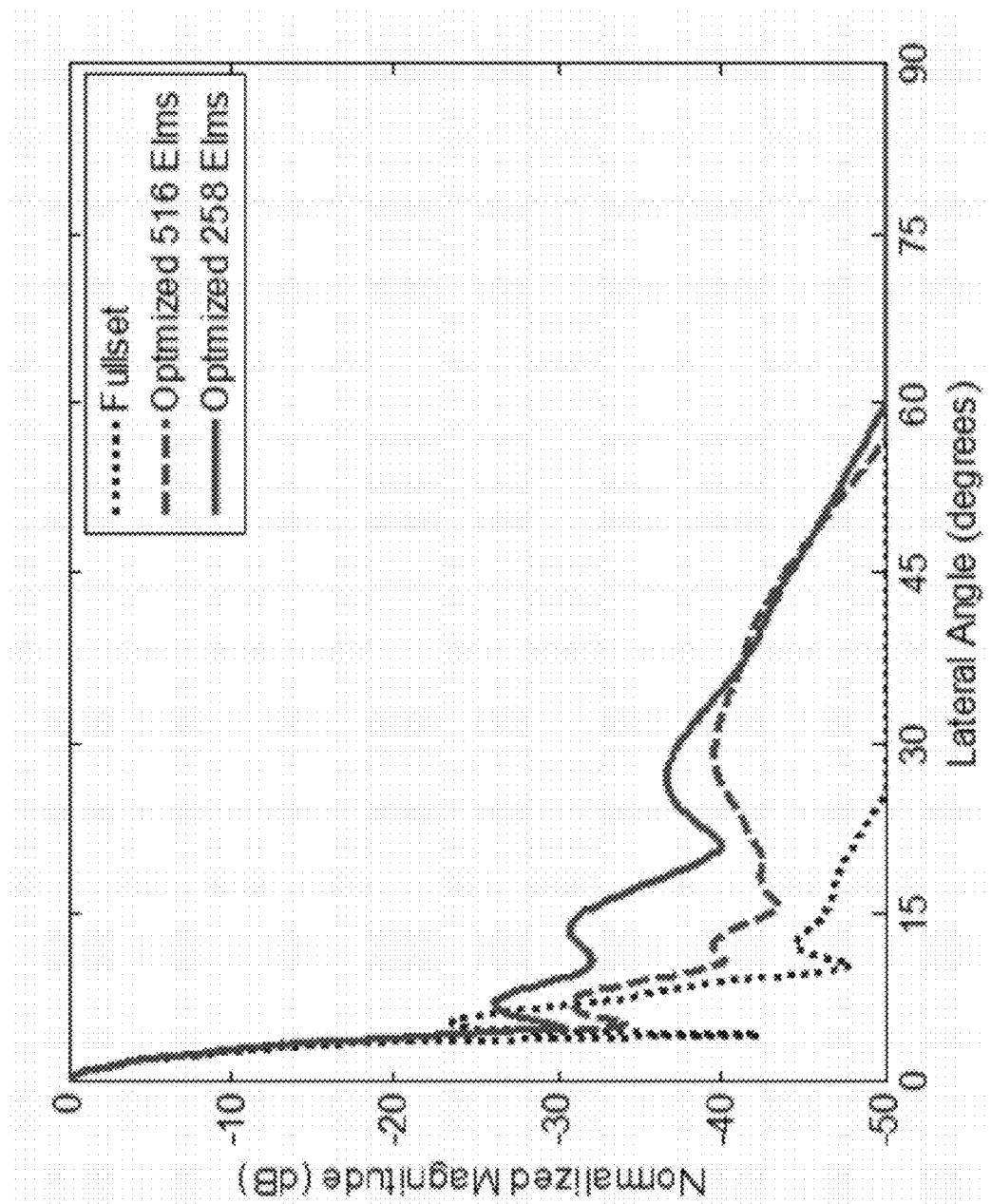

For comparison of the PSF performances, averaged 1-D cross-sectional PSFs are provided in FIG. 14f. The optimized array configurations produce considerably better performance than the full set, though their −6 dB main lobe widths are slightly wider. The lobe widths are likely the result of the extremely sparse structure of the outer elements for the optimized coarray, i.e. the sampling points in the optimized coarray are very far away from each other especially at higher spatial frequencies. In contrast, the full set has identical inter-element distance over the whole coarray space. In addition, for the two optimized cases, especially the case where the firing number is reduced to 516, the first side lobe levels are nearly 5 dB lower when compared to the full set and the grating lobes remain under −40 dB over an angle of approximately 45°. These results show that the simulated annealing algorithm produces excellent results for the optimization of dual hexagonal ring arrays.

Acoustic Cross-Talk

The frequency response of CMUT arrays can be affected by acoustic cross-talk. In other words, individual Tx and Rx elements are affected by nearby Tx and Rx elements resulting in undesired frequency response and time domain, resulting in image distortion. Surface waves present on the CMUT membranes, however, have been identified as the main source of acoustic cross talk. As a result, the mechanical properties of the membranes and the spacing between array elements can improve cross talk performance.

Figure 15:
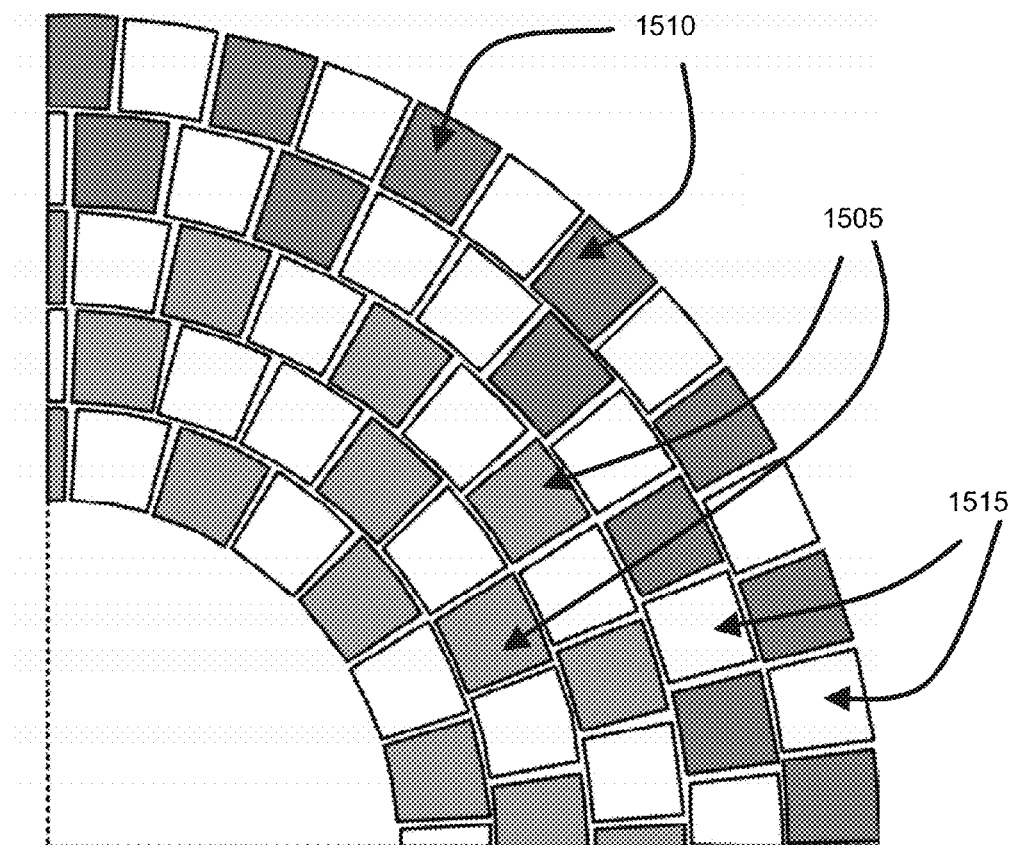
FIG. 15 depicts a chip for a forward-looking ultrasound catheter comprising Tx, Rx, and dummy (Cx) elements, in accordance with some embodiments of the present invention.

Embodiments of the present invention, therefore, can further comprise a CMUT array with dummy, solid (i.e., filled gap, non-moving), or collapsed elements dispersed between active array elements. The sparse array approach described above enables the use of these dummy elements, as shown in FIG. 15, due to the sparse nature of the arrays. In other words, in the space between the active, sparse Tx 1505 and Rx 1510 elements, cross talk reducing dummy elements 1515, or Cx elements, can be implemented. In some embodiments, these Cx elements 1515 can be passive elements and can be, for example and not limitation, solid or collapsed membranes. In other elements, the Cx elements 1515 can be simple active membranes (e.g., membranes with DC bias only such that they do not move). In still other embodiments, the Cx elements 1515 can further comprise mass loading.

Mass loading can be achieved, for example, by fabricating the CMUT membranes with a non-uniform thickness. Mass loading changes the resonant frequency and vibrational characteristics of the CMUT membrane such that they are different from other elements in the imaging array. In this configuration, the array is prevented from having uniform properties, which disrupts the uniform structure that would otherwise tend to support surface waves and surface resonance. The mass loaded membranes can be distributed randomly between Tx 1505 and Rx 1510 CMUT elements to prevent periodicity and strong resonances that may result from periodicity.

Bias Phased Transmission

The flexibility in shaping the CMUT structures, and the resulting availability of external electrical connections due to single chip integration, can also be exploited to improve device performance by increasing transmit power levels. The DC bias levels for Tx elements, for example, can be selected differently from those for Rx elements to improve the overall bandwidth of the imaging system and/or operate these elements in different regimes. Similarly, in some embodiments, different electrode structures can be used for Tx elements to increase the pressure level that can be produced.

Figure 16A:
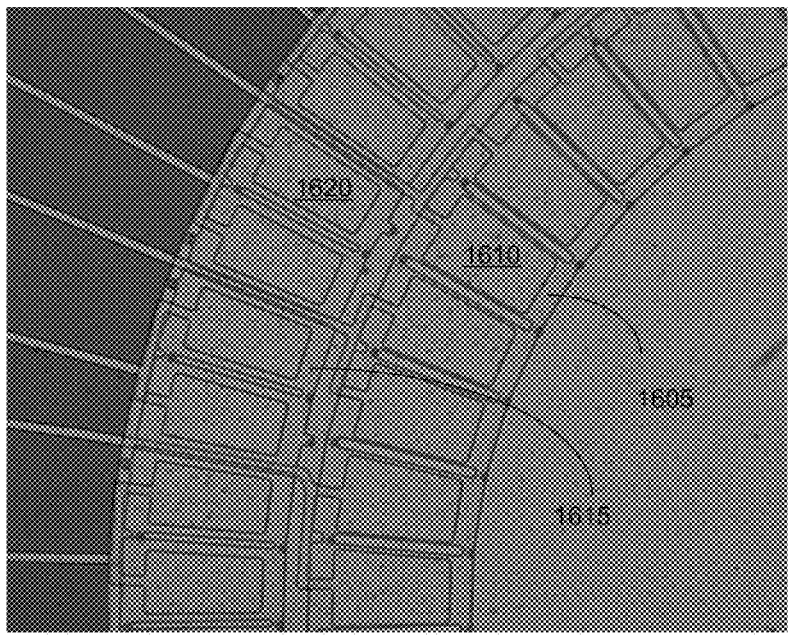
FIGS. 16a-16b depict two possible electrode configurations for the Tx and Rx elements, in accordance with some embodiments of the present invention.
Figure 16B:
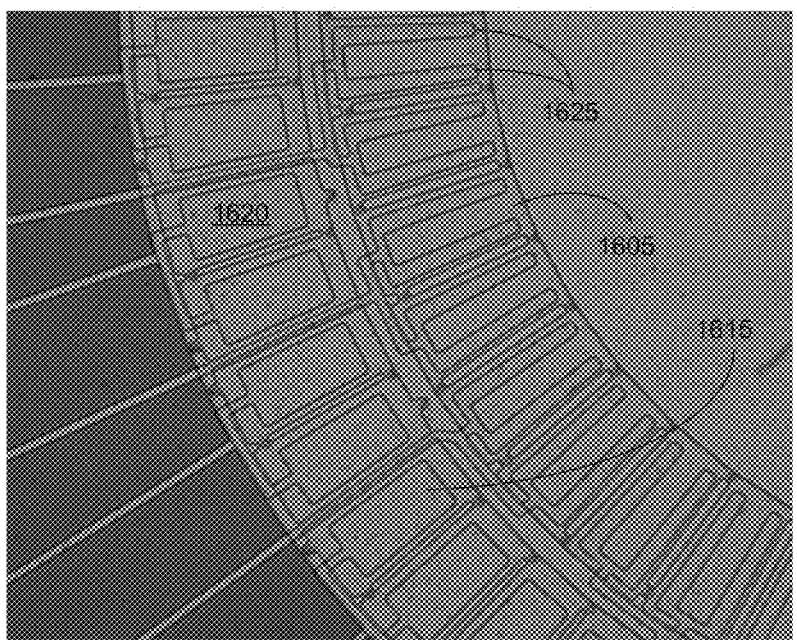

As shown in FIGS. 16a and 16b, in some embodiments, dual-ring CMUT arrays can be used with a variety of electrode configurations. As shown in FIG. 16a, for example, in some embodiments, the TX elements 1605 (inner ring) can have substantially full coverage electrodes 1610 for maximum transmit power, while the Rx elements 1615 (outer ring) can have 70% electrode 1620 coverage to reduce parasitic capacitance. Similarly, as shown in FIG. 16B, dual electrode 1625 Tx elements 1605 can be used with 70% electrode 1620 coverage Rx elements 1615. In either case, the Rx element electrodes 1620 can be optimized for reduced parasitic capacitance, while the Tx element electrodes 1610, 1625 can be optimized to improve acoustic pressure efficiency (i.e., Pa/V) and to maximize output pressure.

The electrode size and bias voltage can also be used to create phased arrays of Tx elements to increase transmission pressure. This approach can be used to control radiation pattern and power levels. In some embodiments, electrode size distribution, DC bias levels, and polarity, among other things, can be used to form bias-phased and smoothed, or apodized, Tx elements. In other words, phase delays can be created between elements in common phase arrays to provide the desired power level and/or beam shape without increasing the complexity of the electronics.

A single chip CMUT array, for example, can have a sufficient number of electrical connections to provide multiple DC bias levels. In this manner, multiple DC bias levels can be applied to Tx elements within the same array to create the desired phase difference between elements. DC bias levels can include different amplitudes, for wave shaping, and/or opposite polarity bias levels to provide in and out of phase transmission between elements. To create a beam with a rounded profile within the hexagonal arrays (described above), for example, a higher bias voltage can be applied to the center element than to the surrounding elements. In this configuration, the center element will fire first followed by the outer elements, thus creating the desired rounded profile as well as applying amplitude apodization. Similarly, bias voltages of different polarities can also be used to alter the initial position, or preload, of each element to produce similar or different wave shapes.

By adjusting the shape or size of the electrode on each element, as shown in FIG. 16, the desired phase delays and amplitude apodizations can essentially be "hardwired" into the chip. In other words, an element with a large electrode will displace farther than an element with a small electrode in reaction to the same applied bias voltage. When the bias voltage is removed, or inverted therefore, a difference in amplitude and a phase delay is created between the two elements. This concept can be used to shape the beam and/or steer the beam. In some embodiments, for example, the phase delay can be used to create an asymmetrical beam for sampling areas not directly in front of the probe.

Finally, multiple CMUT elements can be fired simultaneously, or nearly simultaneously (i.e., batch fired) to increase power output or wave size. In this configuration, the multiple CMUTs can act as a Tx element of substantially the same size as the combined area of the individual CMUT elements. This can be useful, for example, when the probe must image tissue that is a significant distance from the chip.

Figure 17:
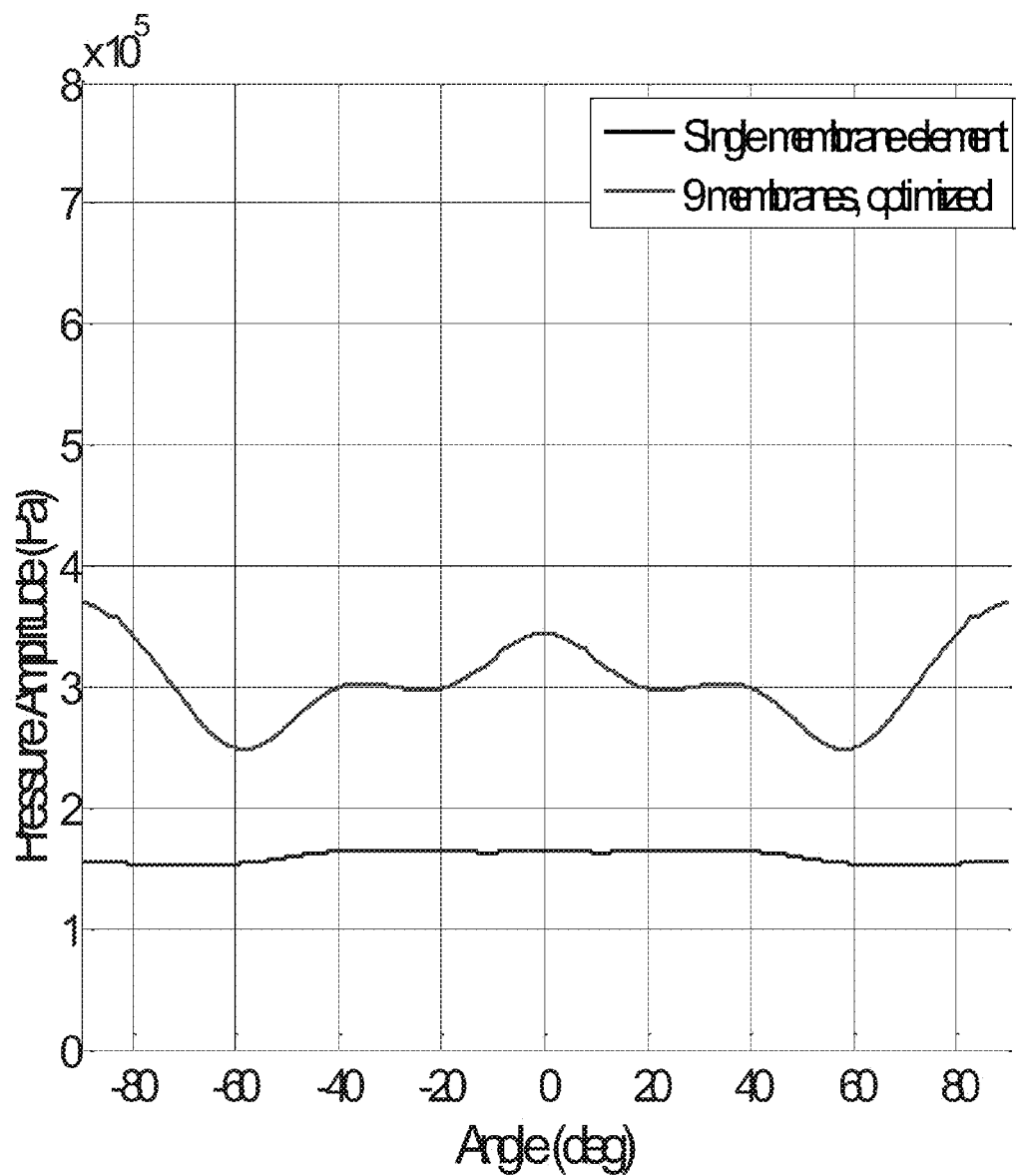
FIG. 17 compares the pressure output of a 9 element Tx subarray and a single membrane element, in accordance with some embodiments of the present invention.

In some embodiments, simulations, such as finite element analysis ("FEA"), related to the fluid coupling at the CMUT surface, can be used to determine a suitable bias level, polarity, and electrode size for the desired beam shape or direction. As shown in FIG. 17, an initial 1-D FEA shows that a nine membrane, bias-phased, and electrode-apodized CMUT, for example, improves the output pressure by 6 dB in the far field as compared to a single membrane CMUT while still covering substantially the entire angular range.

While several possible embodiments are disclosed above, embodiments of the present invention are not so limited. For instance, while several possible components, chip layouts, and phase schemes have been disclosed, other suitable components, materials, and layouts could be selected without departing from the spirit of the invention. In addition, the location and configuration used for various features of embodiments of the present invention can be varied according to a particular application or imaging need that requires a slight variation due to, for example, the materials used and/or space or power constraints. Such changes are intended to be embraced within the scope of the invention.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed embodiments, therefore, are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. A CMUT on CMOS chip for imaging applications comprising:
   a CMOS chip comprising a CMUT array comprising:
      a plurality of CMUT transmit ("Tx") elements;
      a plurality of CMUT receive ("Rx") elements; and
      a plurality of dummy CMUT ("Cx") elements to reduce cross-talk between the plurality of CMUT transmit elements and the plurality of CMUT receive elements; wherein the Cx elements comprise solid CMUT elements.

2. The CMUT on CMOS chip of claim 1, wherein the CMUT on CMOS chip is connected to one or more outputs disposed proximate the back side of the chip with flex tape.

3. The CMUT on CMOS chip of claim 1, wherein at least a portion of the plurality of CMUT Tx elements are disposed in two or more concentric rings to form a defocused annular array.

4. A CMUT on CMOS chip for imaging applications comprising:
   a CMOS chip comprising:
      a plurality of CMUT transmit ("Tx") elements; and
      a plurality of CMUT receive ("Rx") elements;
   wherein the Tx elements are disposed in a first, substantially hexagonal, array on the CMOS chip;
   wherein the Rx elements are disposed in a second, substantially hexagonal, array on the CMOS chip;
   wherein the first array comprises:
      k central CMUT Tx elements; and
      6 k peripheral CMUT Tx elements;
      wherein k≥1 and an integer; and
      wherein the peripheral CMUT Tx elements are disposed in a substantially hexagonal array around the central CMUT Tx elements;
   wherein the central CMUT Tx elements each comprise a central element electrode;
   wherein the peripheral CMUT Tx elements each comprise a peripheral element electrode; and
   wherein the central elements electrode(s) are connected to a first circuit and the peripheral element electrode(s) are connected to a second circuit to create a phase shift, a difference in amplitude, or both between the central CMUT Tx elements and the peripheral CMUT Tx elements.

5. The CMUT on CMOS chip of claim 4, wherein the number of CMUT elements in the first and second arrays is a multiple of 6.

6. The CMUT on CMOS chip of claim 4, wherein the first array is disposed concentrically inside the second array.

7. The CMUT on CMOS chip of claim 4, wherein the second array is disposed concentrically inside the first array.

8. The CMUT on CMOS chip of claim 4, wherein two or more of the Tx elements in the first array can be batch fired to increase the transmit power of the first array.

9. The CMUT on CMOS chip of claim 4, wherein at least a portion of the plurality of CMUT elements in the hexagonal Tx array are disposed in two or more concentric rings to form a defocused annular array.

10. The CMUT on CMOS chip of claim 4, wherein the central elements electrode(s) are larger than the peripheral element electrode(s).

11. The CMUT on CMOS chip of claim 4, wherein the Tx element electrodes each comprise dual electrodes.

12. The CMUT on CMOS chip of claim 4,
   wherein the Tx element electrodes are sized and shaped to substantially cover the Tx elements; and
   wherein the Rx elements electrodes are sized and shaped to cover between approximately 50%-80% of the Rx elements.

13. A method comprising:
   selecting a subset from an array of transmit ("Tx") elements and receive ("Rx") elements of a CMUT array on a CMOS chip to reduce a number of element firings for imaging, the CMUT array comprising:
      a plurality of CMUT transmit ("Tx") elements; and
      a plurality of CMUT receive ("Rx") elements;
   wherein selecting the subset comprises:
      determining a portion of Tx elements of the plurality of CMUT Tx elements and a portion of Rx elements of the plurality of CMUT Rx elements that uniformly fill an available coarray space, while eliminating redundant Tx elements and Rx elements that do not improve imaging resolution of the CMUT array on the CMOS chip.

14. The method of claim 13, wherein the determining is computed by synthetic array processing.

15. The method of claim 13, wherein the determining is computed by simulated annealing.

16. The method of claim 13, wherein the determining is computed with a point spread function.

17. The method of claim 16, wherein computing the point spread function comprises minimizing an energy function associated with a peak side lobe level.

18. The method of claim 16, wherein the point spread function is represented by:

$$H(r, \theta, \varphi) = \sum_i w_i \cdot \sum_j w_j \cdot s\left(\frac{2r}{c} - t_i - t_j - \tau_i - \tau_j\right)$$

wherein:
   $(r,\theta,\varphi)$ are the spherical coordinates;
   i and j represent Tx element and Rx element indices respectively;
   s(.) is an excitation pulse;
   c is the speed of sound;

$t_i$ and $t_j$ are flight times between a point target and the Tx and Rx elements respectively;

$\tau_i$ and $\tau_j$ are corresponding focusing delay times; and $w_i$ and $w_j$ represent weighting coefficients.

19. The method of claim 18, wherein the weighting coefficients $w_i$ and $w_j$ are set to unity.

20. The method of claim 18, wherein one or more of obliquity and attenuation effects associated with the Tx element and Rx element are ignored.

\* \* \* \* \*